United States Patent
Fritze et al.

(10) Patent No.: US 7,241,903 B2
(45) Date of Patent: Jul. 10, 2007

(54) METALLOCENES, USE IN CATALYST SYSTEM FOR PRODUCING OLEFIN POLYMERS

(75) Inventors: Cornelia Fritze, Frankfurt (DE); Luigi Resconi, Ferrara (IT); Jörg Schulte, Frankfurt (DE); Simona Guidotti, Malalbergo (IT)

(73) Assignee: Basell Polyolefine GmbH, Wesseling (DE)

( * ) Notice: Subject to any disclaimer, the term of this patent is extended or adjusted under 35 U.S.C. 154(b) by 745 days.

(21) Appl. No.: 10/481,372

(22) PCT Filed: Jun. 20, 2002

(86) PCT No.: PCT/EP02/07093

§ 371 (c)(1),
(2), (4) Date: Dec. 18, 2003

(87) PCT Pub. No.: WO03/000106

PCT Pub. Date: Jan. 3, 2003

(65) Prior Publication Data

US 2004/0171855 A1 Sep. 2, 2004

(30) Foreign Application Priority Data

Jun. 22, 2001 (EP) .................................. 01202413

(51) Int. Cl.
*C07F 17/00* (2006.01)
*B01J 31/38* (2006.01)
*C08F 4/44* (2006.01)

(52) U.S. Cl. .............................. 549/2; 549/43; 549/60; 549/206; 549/209; 549/212; 549/458; 548/402; 546/2; 546/10; 556/11; 556/12; 502/117; 502/132; 502/152; 526/160; 526/161; 526/171; 526/351; 526/943

(58) Field of Classification Search .................... 549/2, 549/43, 60, 206, 209, 212, 458; 556/11, 556/12; 502/117, 132, 152; 526/160, 161, 526/171, 351, 943; 546/2, 10; 548/402
See application file for complete search history.

(56) References Cited

U.S. PATENT DOCUMENTS

| | | | |
|---|---|---|---|
| 6,444,606 B1 | 9/2002 | Bingel et al. | 502/152 |
| 6,620,888 B2 * | 9/2003 | Resconi et al. | 525/210 |
| 7,112,638 B2 * | 9/2006 | Nifant'ev et al. | 526/160 |
| 7,166,683 B2 * | 1/2007 | Resconi | 526/161 |
| 2003/0008984 A1 | 1/2003 | Kratzer et al. | 526/127 |
| 2003/0013913 A1 | 1/2003 | Schottek et al. | 564/8 |
| 2005/0222349 A1 * | 10/2005 | Fait et al. | 526/127 |
| 2006/0167195 A1 * | 7/2006 | Resconi et al. | 526/129 |
| 2006/0235173 A1 * | 10/2006 | Resconi | 526/127 |

FOREIGN PATENT DOCUMENTS

| | | |
|---|---|---|
| DE | 19962910 | 4/2001 |
| DE | 19962814 | 6/2001 |
| EP | 0633272 | 1/1995 |
| WO | 9102012 | 2/1991 |
| WO | 9200333 | 1/1992 |
| WO | 9525757 | 9/1995 |
| WO | 9532995 | 12/1995 |
| WO | 9822486 | 5/1998 |
| WO | 9840331 | 9/1998 |
| WO | 9840416 | 9/1998 |
| WO | 9840419 | 9/1998 |
| WO | 9921899 | 5/1999 |
| WO | 9936427 | 7/1999 |
| WO | 0121674 | 3/2001 |
| WO | 0147939 | 7/2001 |
| WO | 0148040 | 7/2001 |
| WO | 0162764 | 8/2001 |
| WO | 0170878 | 9/2001 |
| WO | 02083699 | 10/2002 |
| WO | 02092564 | 11/2002 |

OTHER PUBLICATIONS

E. Hey-Hawkins, "Bis(cyclopentadienyl)zirconium(IV) or -hafnium(IV) Compounds with Si-, Ge-, Sn-, N-, P-, As-, Sb-, O-, S-, Se-, Te-, or Transition Metal-Centered Anionic Ligands;" *Chem. Rev.*, vol. 94 (6), p. 1661-1717 (1994).

* cited by examiner

*Primary Examiner*—Porfirio Nazario-Gonzalez
(74) *Attorney, Agent, or Firm*—William R Reid

(57) ABSTRACT

A metallocene compound of formula (I): wherein M is zirconium, titanium and hafnium; X is a hydrogen atom, a halogen atom or a hydrocarbon radical; $R^1$ is a linear $C_1$-$C_{20}$-alkyl radical; $R^2$ is a hydrogen atom or hydrocarbon $R^3$, $R^4$, $R^5$, $R^6$, $R^7$, and $R^8$, are hydrogen atoms or hydrocarbon radicals, A is a sulphur (S) atom or an oxygen (O) atom; Q is a radical of formula (II), (III) or (IV) being bonded to the indenyl at the position indicated by the symbol *; (II), (III), (IV) wherein $T^1$ is a sulphur atom, an oxygen (O) atom or a NR; $R^9$, $R^{10}$ and $R^{11}$ are hydrogen atoms or hydrocarbon radicals; $T^2$, $T^3$, $T^4$, $T^5$, and $T^6$ are carbon atoms (C) or nitrogen atoms (N); $m^1$, $m^2$, $m^3$, $m^4$ and $m^5$ are 0 or 1; $R^{12}$, $R^{13}$, $R^{14}$, $R^{15}$ and $R^{16}$ are hydrogen atoms or hydrocarbon radicals with the provisos that at least one of $R^{12}$, $R^{13}$, $R^{14}$, $R^{15}$ and $R^{16}$ is different from hydrogen atoms, and that no more than two of $T^2$, $T^3$, $T^4$, $T^5$ and $T^6$ are nitrogen atoms.

23 Claims, No Drawings

METALLOCENES, USE IN CATALYST SYSTEM FOR PRODUCING OLEFIN POLYMERS

This application is the U.S. national phase of International Application PCT/EP02/07093, filed Jun. 20, 2002.

The present invention relates to a new class of metallocene compounds, to catalysts based thereon and to a process carried out in the presence of said catalysts for the preparation of polymers of alpha-olefins, particularly of propylene polymers. The present invention also relates to the ligands for those metallocenes.

Products of propylene homopolymerization can have varying degrees of crystallinity. The type and amount of crystallinity is largely dependent on the microstructure of the polypropylene. Polypropylene having predominantly isotactic or syndiotactic structure is partially crystalline, while polypropylene having predominantly atactic structure is amorphous.

Metallocene catalysts have recently been used in the polymerization reaction of olefins. Operating in the presence of these catalysts, polymers characterized by a narrow molecular weight distribution and having structural characteristics of interest have been obtained. By polymerizing propylene in the presence of metallocene catalysts, amorphous or highly crystalline polypropylenes can be obtained depending on the metallocene used.

Certain metallocene catalysts are also known that can produce partially crystalline elastomeric polypropylene. International application WO 95/25757, for instance, describes unbridged metallocene catalysts that can produce isotactic-atactic stereoblock polypropylenes having elastomeric thermoplastic properties. Despite the homogeneity in molecular weight distribution, the tacticity distribution of these polymers is not homogeneous. Moreover, the activity is low.

Recently, heterocyclic metallocene compounds have been used in the polymerization of alpha-olefins. International application WO 98/22486 discloses a class of metallocenes containing a cyclopentadienyl radical directly coordinating the central metal atom, to which are fused one or more rings containing at least one heteroatom. These metallocenes, in combination with a suitable cocatalyst, are used in the polymerization of olefins such as propylene. The working examples relate to the preparation of highly stereoregular polypropylene. More recently in WO 01/47939 in the name of the same applicant a new class of heterocyclic metallocene has been disclosed.

It would be desirable to provide a novel class of metallocenes which, when used in catalysts for the polymerization of olefins, in particular of propylene, are capable of yielding polymers endowed with high molecular weights, high melting point, narrow molecular weight distribution and a reduced degree of crystallinity. It would be most desirable to provide metallocene catalysts that can produce those polymers with high activity, such that the amount of catalyst remaining in the formed polymer is minimized.

A novel class of metallocene compounds has now been unexpectedly found, which achieves the above and other results.

According to a first aspect the present invention provides a metallocene compound of formula (I):

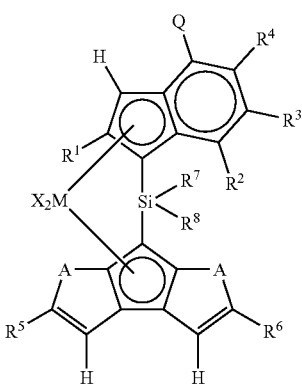

wherein

M is selected from the group consisting of zirconium, titanium and hafnium; preferably M is zirconium or hafnium; more preferably M is zirconium;

X, same or different, is a hydrogen atom, a halogen atom, a R, OR, OR'O, $OSO_2CF_3$, OCOR, SR, $NR_2$ or $PR_2$ group, wherein the R substituents are linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylakyl radicals, optionally containing one or more heteroatoms belonging to groups 13-17 of the Periodic Table of the Elements; and the R' substituent is a divalent radical selected from the group consisting of $C_1$-$C_{20}$-alkylidene, $C_6$-$C_{20}$-arylidene, $C_7$-$C_{20}$-alkylarylidene, $C_7$-$C_{20}$-arylalkylidene; preferably X is a halogen atom, a R, OR' O or OR group; more preferably X is chlorine or methyl;

$R^1$ is a linear $C_1$-$C_{20}$-alkyl radical; preferably $R^1$ is methyl or ethyl;

$R^2$ is a hydrogen atom or a linear or branched, saturated or unsaturated $C_1$-$C_{20}$-alkyl radical;

$R^3$ and $R^4$ same or different are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements, or they can form together a condensed saturated or unsaturated 5 or 6 membered ring, optionally containing one or more heteroatoms belonging to groups 13-16 of the Periodic Table of the Elements, said ring optionally bearing one or more substituents; preferably $R^3$ and $R^4$ are hydrogen atoms, methyl or they form a condensed saturated or unsaturated 5 or 6 membered ring;

$R^5$ and $R^6$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; preferably $R^5$ and $R^6$ are a $C_1$-$C_{20}$-alkyl radicals; more preferably they are methyl;

$R^7$ and $R^8$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; preferably $R^7$ and $R^8$ are $C_1$-$C_{20}$-alkyl or $C_6$-$C_{20}$-aryl radicals; more preferably they are methyl, or phenyl;

A, same or different, is a sulphur (S) atom or an oxygen (O) atom; preferably A is sulphur;

Q is a radical of formula (II), (III) or (IV) being bonded to the indenyl at the position marked with the symbol *;

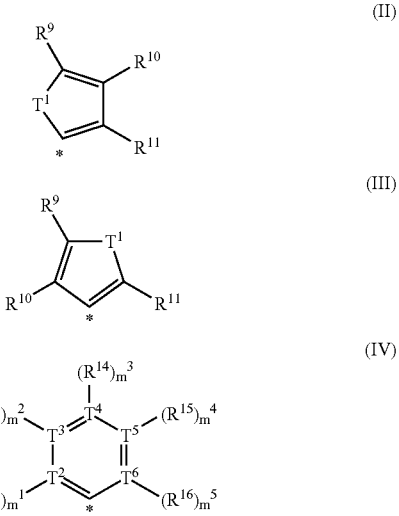

wherein $T^1$ is a sulphur (S) atom, an oxygen (O) atom or a NR group R being defined as above; preferably the group NR is N-methyl, N ethyl, N-tertbutyl or N-phenyl group; preferably $T^1$ is oxygen or sulphur; more preferably $T^1$ is sulphur;

$R^9$, $R^{10}$ and $R^{11}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or $R^9$ and $R^{10}$ can form together a condensed saturated or unsaturated 5 or 6 membered ring, optionally containing one or more heteroatoms belonging to groups 13-16 of the Periodic Table of the Elements, said ring optionally bearing one or more substituents;

preferably $R^{11}$ is a hydrogen atom, preferably $R^9$ and $R^{10}$ are a linear or branched, saturated or unsaturated $C_1$-$C_{20}$-alkyl radical or they from a condensed saturated or unsaturated 5 or 6 membered ring, optionally containing one or more heteroatoms belonging to groups 13-16 of the Periodic Table of the Elements, said ring optionally bearing one or more substituents; more preferably $R^9$ and $R^{10}$ form a condensed benzene ring optionally bearing one or more substituents;

$T^2$, $T^3$, $T^4$, $T^5$ and $T^6$, same or different, are carbon atoms (C) or nitrogen atoms (N);

$m^1$, $m^2$, $m^3$, $m^4$ and $m^5$ are 0 or 1; more precisely each of $m^1$, $m^2$, $m^3$, $m^4$ and $m^5$ is 0 when the correspondent $T^2$, $T^3$, $T^4$, $T^5$ and $T^6$ is a nitrogen atom and is 1 when the correspondent $T^2$, $T^3$, $T^4$, $T^5$ and $T^6$ is a carbon atom;

$R^{12}$, $R^{13}$, $R^{14}$, $R^{15}$ and $R^{16}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or two vicinal $R^{12}$, $R^{13}$, $R^{14}$, $R^{15}$ can form together a condensed saturated or unsaturated 5 or 6 membered ring, optionally containing one or more heteroatoms belonging to groups 13-16 of the Periodic Table of the Elements, said ring optionally bearing one or more substituents; with the provisos that at least one of $R^{12}$, $R^{13}$, $R^{14}$, $R^{15}$ and $R^{16}$ is different from hydrogen atom, and that no more than two of $T^2$, $T^3$, $T^4$, $T^5$ and $T^6$ are nitrogen atoms;

A preferred radical belonging to formula (IV) has formula (IVa) being bonded to the indenyl at the position indicated by the symbol *:

wherein $R^{14}$ is described above with the proviso that it is different from hydrogen atom; preferably $R^{14}$ is a branched, saturated or unsaturated $C_1$-$C_{20}$-alkyl or $C_6$-$C_{20}$-aryl radical; more preferably $R^{14}$ is a phenyl group, optionally substituted with one or more alkyl groups, or a group of formula $C(R^{17})_3$ wherein $R^{17}$, same or different, is a linear or branched, saturated or unsaturated $C_1$-$C_{20}$-alkyl radical; preferably $R^{17}$ is methyl.

A further preferred radical belonging to formula (IV) has formula (IVb) being bonded to the indenyl at the position indicated by the symbol *:

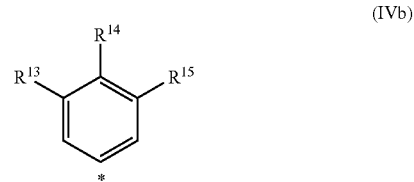

wherein $R^{13}$ and $R^{15}$, are described above with the proviso that they are different from hydrogen atoms; preferably $R^{13}$ and $R^{15}$ are a branched, saturated or unsaturated $C_1$-$C_{20}$-alkyl or a $CF_3$ radical; more preferably they are a group of formula $C(R^{17})_3$ wherein $R^{17}$ has been described above;

$R^{14}$ is a hydrogen atom or a $R^{18}$ or $OR^{18}$ group, wherein $R^{18}$ is a linear or branched, saturated or unsaturated $C_1$-$C_{20}$-alkyl or $C_6$-$C_{20}$-aryl radical optionally containing one or more heteroatoms belonging to groups 13-17 of the Periodic Table of the Elements; preferably $R^{14}$ is a hydrogen atom or a $OR^{18}$ group, preferably $R^{18}$ is a linear or branched, saturated or unsaturated $C_1$-$C_{20}$-alkyl or $C_6$-$C_{20}$-aryl radical.

A further preferred radical belonging to formula (IV) has formula (IVc) being bonded to the indenyl at the position indicated by the symbol *:

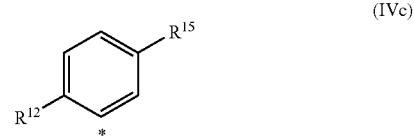

wherein $R^{12}$ and $R^{15}$ are described above with the proviso that they are different from hydrogen atoms; preferably $R^{12}$ and $R^{15}$ are a linear, saturated or unsaturated $C_1$-$C_{20}$-alkyl radical; more preferably they are methyl.

A further preferred radical belonging to formula (IV) has formula (IVd) being bonded to the indenyl at the position indicated by the symbol *:

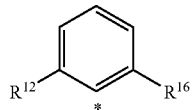

(IVd)

wherein $R^{12}$ and $R^{16}$ are described above with the proviso that they are different from hydrogen atoms; preferably $R^{12}$ and $R^{16}$ are a linear, saturated or unsaturated $C_1$-$C_{20}$-alkyl radicals; more preferably they are methyl.

A further preferred radical belonging to formula (IV) has formula (IVe) being bonded to the indenyl at the position indicated by the symbol *:

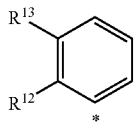

(IVe)

wherein $R^{12}$ and $R^{13}$ are described above with the proviso that they are different from hydrogen atoms; preferably $R^{12}$ and $R^{13}$ are a linear, saturated or unsaturated $C_1$-$C_{20}$-alkyl radical, or they can form a saturated or unsaturated condensed 5 or 6 membered ring optionally containing one or more heteroatoms belonging to groups 13-16 of the Periodic Table of the Elements, said ring optionally bearing one or more substituents; more preferably $R^{12}$ and $R^{13}$ form a saturated or unsaturated condensed 5 or 6 membered ring optionally containing one or more heteroatoms belonging to groups 15-16 of the Periodic Table of the Elements such as a phenyl ring, a pentadiene ring or a naphtalene ring.

A further preferred radical belonging to formula (IV) has formula (IVf) being bonded to the indenyl at the position indicated by the symbol *:

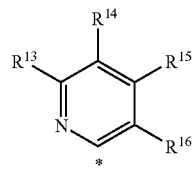

(IVf)

wherein $R^{13}$, $R^{14}$, $R^{15}$ and $R^{16}$ are described as above with the proviso that at least one among $R^{13}$, $R^{14}$, $R^{15}$ and $R^{16}$ is different from a hydrogen atom; preferably $R^{15}$ and $R^{16}$ are hydrogen atoms; preferably $R^{13}$ and $R^{14}$ are a linear or branched, saturated or unsaturated $C_1$-$C_{20}$-alkyl radical, or they form a saturated or unsaturated condensed 5 or 6 membered ring optionally containing one or more heteroatoms belonging to groups 13-16 of the Periodic Table of the Elements, said ring optionally bearing one or more substituents; more preferably $R^{13}$ and $R^{14}$ form a saturated or unsaturated condensed 5 or 6 membered ring optionally containing one or more heteroatoms belonging to groups 15-16 of the Periodic Table of the Elements.

Preferably the metallocene compounds of formula (I) have formula (Ia) or (Ib):

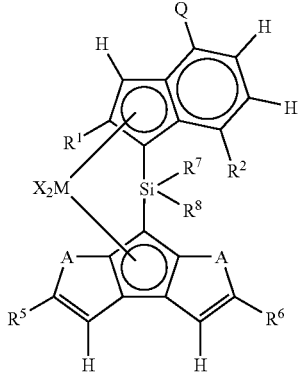

(Ia)

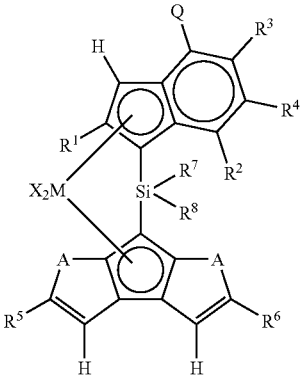

(Ib)

wherein M, X, $R^1$, $R^5$, $R^6$, $R^7$, $R^8$, A and Q have been described above; $R^2$ is a linear or branched, saturated or unsaturated $C_1$-$C_{20}$-alkyl radical; preferably $R^2$ is methyl;

$R^3$ and $R^4$ form together a condensed saturated 5 or 6 membered aliphatic ring;

Non limitative examples of compounds of formula (I) are:

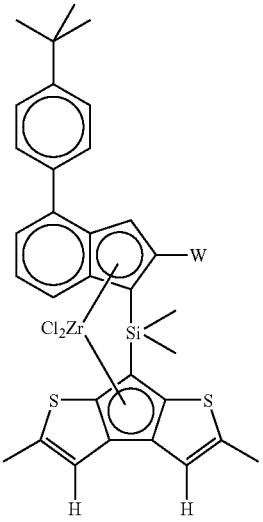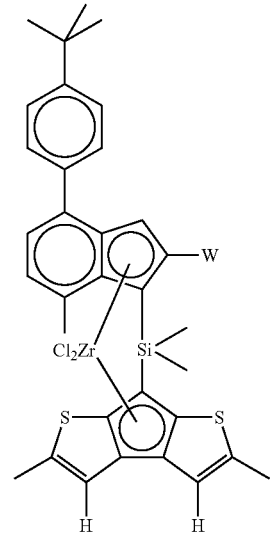

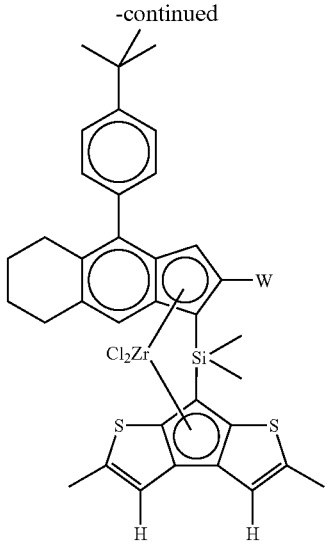
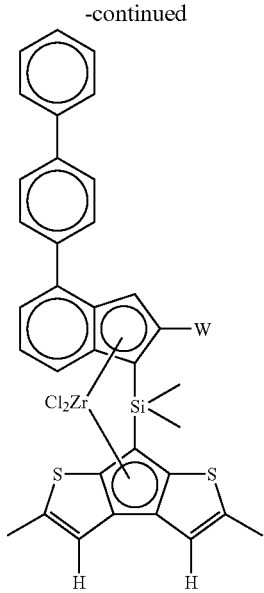
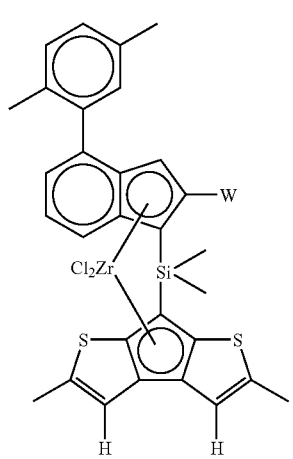
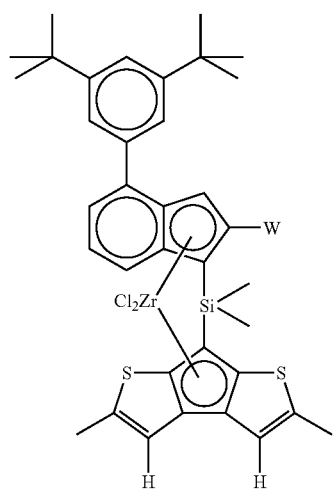
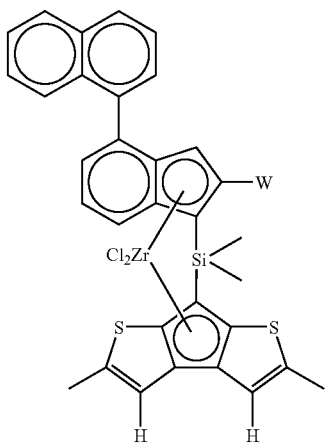
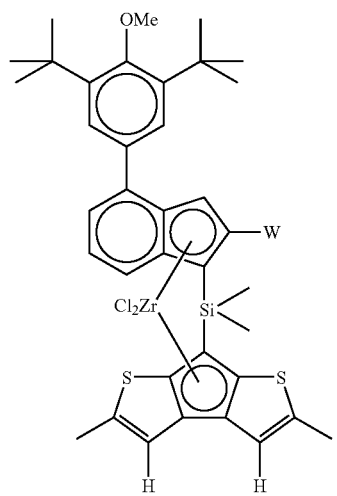

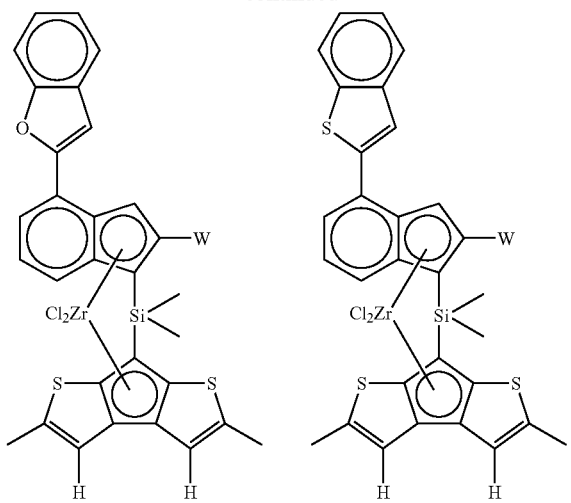
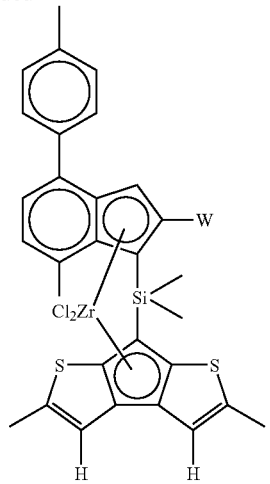

wherein W is methyl or ethyl; as well as the corresponding zirconium dimethyl complexes;

A further object of the present invention is a ligand of formula (V) that can be suitable used as intermediate for the preparation of metallocenes of formula (I).

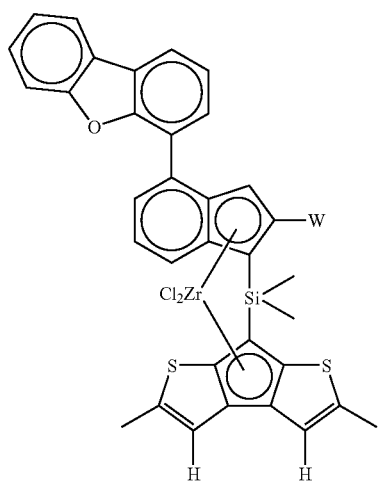

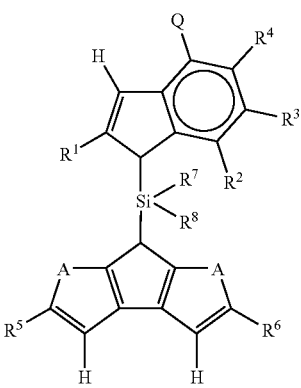
(V)

and its double bond isomer;

wherein $R^1$, $R^2$, $R^3$, $R^4$, $R^5$, $R^6$, $R^7$, $R^8$, A and Q have been described above.

This ligand can be prepared according to a process comprising the following steps:

a) contacting a compound of the formula (VI)

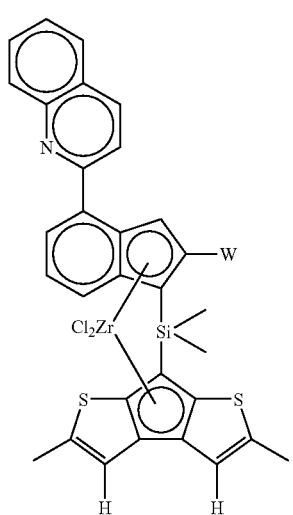
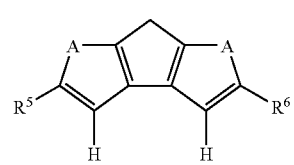
(VI)

with a base selected from the group consisting of metallic sodium and potassium, sodium and potassium hydroxide, organolithium compound and an organomagnesium compound wherein the molar ratio between the compound of the formula (VI) and said base is at least 1:1 b) contacting the anionic compounds obtained from step a) with a compound of formula (VII):

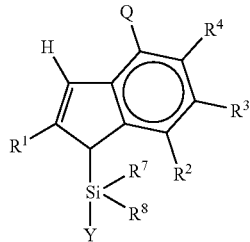

wherein Y is a halogen radical selected from the group consisting of chloride, bromide and iodide, preferably chlorine and bromine.

An alternative process for preparing the ligand of formula (V) comprises the following steps:

a) contacting a compound of the formula (VIII)

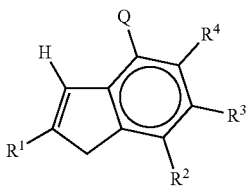

with a base selected from the group consisting of metallic sodium and potassium, sodium and potassium hydroxide, an organolithium compound and an organomagnesium compound, wherein the molar ratio between the compound of the formula (VIII) and said base is at least 1:1;

b) contacting the anionic compounds obtained from step a) with a compound of formula (IX):

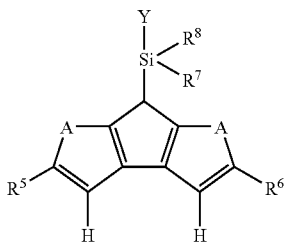

wherein Y is a halogen radical selected from the group consisting of chloride, bromide and iodide, preferably chlorine and bromine.

The base used in step a) of both processes is preferably methyllithium or n-butyllithium. All the reactions are carried out in aprotic solvents. Non limiting examples of aprotic solvents suitable for the above reported processes are tetrahydrofurane, dimethoxyethane, diethylether, toluene, dichloromethane pentane, hexane and benzene.

During the whole processes, the temperature is generally kept between $-100°$ C. and $80°$ C., preferably between $-20°$ C. and $40°$ C.

Compounds of formula (VI), (VII), (VIII) and (IX) are known in the art. In particular compounds of formula (VI) and (IX) can be prepared according to the process described in PCT/EP00/13191 or EP 01201821.4. Compounds of formula (VII) and (VIII) can be prepared a described in WO 9840331, WO 9840419 and WO 9840416.

Compounds of formula (V) can be suitable used as intermediates for the preparation of metallocenes of formula (I).

Therefore, a process for the preparation of a metallocene compound of formula (I), comprises the steps of contacting the ligand of formula (V), with a compound capable of forming the corresponding dianionic compound and thereafter with a compound of general formula $MX_4$, wherein M and X are defined as above.

The compound able to form said corresponding dianionic compound is selected from the group consisting of hydroxides of alkali- and alkaline-earth metals, metallic sodium and potassium, organometallic lithium salts or organomagnesium compounds (Grignard reagent). Preferably, the compound able to form said corresponding dianionic compound is hexillithium, butyllithium or methyllithium.

Non-limiting examples of compounds of formula $MX_4$ are titanium, zirconium and hafnium tetrachloride.

More specifically, the ligand of formula (V) is dissolved in a polar aprotic solvent and to the obtained solution is added a solution of an organolithium compound in an apolar solvent. The thus obtained anionic compound is optionally separated, dissolved or suspended in a polar aprotic solvent and thereafter added to a suspension of the compound $MX_4$ in a polar aprotic solvent. At the end of the reaction, the solid product obtained is separated from the reaction mixture by techniques commonly used in the state of the art such as filtration or recrystallization. Non limiting examples of polar aprotic solvents suitable for the above reported processes are tetrahydrofurane, dimethoxyethane, diethylether and dichloromethane. Non limiting examples of apolar solvents suitable for the above process are pentane, hexane, benzene and toluene.

Throughout the process, the temperature is generally kept between $-100°$ C. and $80°$ C., preferably between $-20°$ C. and $40°$ C.

An alternative process for preparing the compounds of formula (I) wherein at least one X is halogen is described in EP 01201327.2.

In the case in which at least one substituent X in the metallocene compound of the formula (I) is different from halogen an alternative process for preparing it consists in preparing the dihalogen derivative, i.e. the complex wherein both X substituents are halogen, and then substituting the halogen atoms with the appropriate X groups by the methods generally known in the art. For example, if the desired substituents X are alkyl groups, the metallocenes can be made by reaction with organomagnesium compound (Grignard reagents) or with alkyllithium compounds. General methods for substituting X with substituents other than halogen such as sulfur, phosphorus, oxygen, etc. are described in Chem. Rev. 1994, 94, 1661-1717, and the cited references therein. An alternative process for preparing the compounds of formula (I) wherein at least one X is alkyl is described in WO 99/36427.

Another object of the present invention is a catalyst for the polymerization of alpha-olefins obtainable by contacting:

a) a metallocene compound of formula (I):

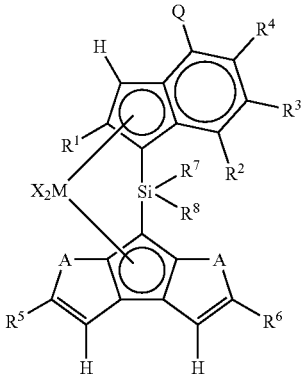

(I)

wherein M, X, $R^1$, $R^2$, $R^3$, $R^4$, $R^5$, $R^6$, $R^7$, $R^8$, A and Q have been described above;

b) an alumoxane or a compound able to form an alkyl-metallocene cation; and c) optionally an organo aluminum compound.

Alumoxanes used as component b) can be obtained by reacting water with an organo-aluminium compound of formula $H_jAlU_{3-j}$ or $H_jAl_2U_{6-j}$, where U substituents, same or different, are hydrogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radical, optionally containing silicon or germanium atoms with the proviso that at least one U is different from halogen, and j ranges from 0 to 1, being also a non-integer number. In this reaction the molar ratio of Al/water is preferably comprised between 1:1 and 100:1.

The molar ratio between aluminium and the metal of the metallocene is comprised between about 10:1 and about 20000:1, and more preferably between about 100:1 and about 5000:1.

The alumoxanes used in the catalyst according to the invention are considered to be linear, branched or cyclic compounds containing at least one group of the type:

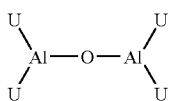

wherein the substituents U, same or different, are described above.

In particular, alumoxanes of the formula:

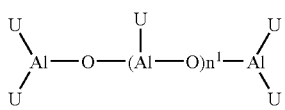

can be used in the case of linear compounds, wherein $n^1$ is 0 or an integer from 1 to 40 and the substituents U are defined as above, or alumoxanes of the formula:

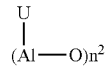

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in PCT/EP00/09111 in which the alkyl and aryl groups have specific branched patterns.

Non-limiting examples of aluminium compounds according to said PCT applications are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl) aluminium (TTUMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (D and $E^-$ is a compatible anion, which is able to stabilize the active catalytic species originating from the reaction of the two compounds, and which is sufficiently labile to be able to be removed by an olefinic monomer. Preferably, the anion $E^-$ comprises of one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred examples of these compounds are described in WO 91/02012. Moreover, compounds of the formula $BAr_3$ can conveniently be used.

Compounds of this type are described, for example, in the published International patent application WO 92/00333. Other examples of compounds able to form an alkylmetallocene cation are compounds of formula BAR$_3$P wherein P is a substituted or unsubstituted pyrrol radicals. These compounds are described in PCT/EP01/01467. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula D$^+$E$^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylani liniumtetra(phenyl)borate,
N,N-Diethylaniliniumtetra(phenyl)borate,
N,N-Dimethylaniliniumtetrakis(pentafluorophenyl)boratee,
N,N-Dimethylaniliniumtetrakis(pentafluorophenyl)aluminate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate,
N,N-Dimethylaniliniumtetrakis(pentafluorophenyl)borate.

Organic aluminum compounds used as compound c) are those of formula H$_j$AlU$_{3-j}$ or H$_j$Al$_2$U$_{6-j}$ described above.

The catalysts of the present invention can also be supported on an inert carrier. This is achieved by depositing the metallocene compound a) or the product of the reaction thereof with the component b), or the component b) and then the metallocene compound a) on an inert support such as, for example, silica, alumina, Al—Si, Al—Mg mixed oxides, magnesium halides, styrene/divinylbenzene copolymers, polyethylene or polypropylene. The supportation process is carried out in an inert solvent such as hydrocarbon for example toluene, hexane, pentane or propane and at a temperature ranging from 0° C. to 100° C., preferably the process is carried out at a temperature ranging from 20° C. to 80° C.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633272.

Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

The solid compound thus obtained, in combination with the further addition of the alkylaluminium compound either as such or prereacted with water if necessary, can be usefully employed in the gas-phase polymerization.

Another object of the present invention is a process for polymerizing one or more alpha-olefins of formula CH$_2$=CHZ, wherein Z is hydrogen or a C$_1$-C$_{20}$ alkyl group, comprising the step of contacting under polymerization conditions one or more of said alpha-olefins with a catalyst system obtainable by contacting:

a) a metallocene compound of formula (I):

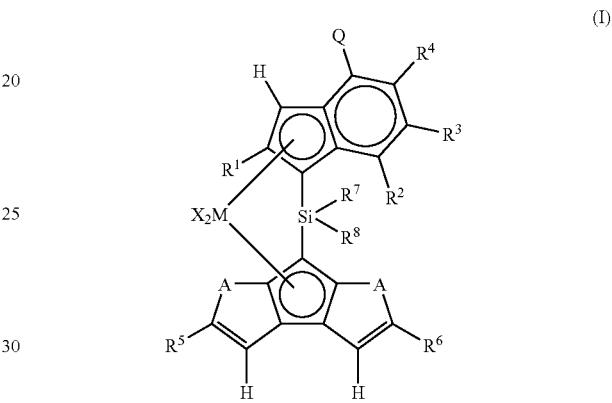

(I)

wherein M, X, R$^1$, R$^2$, R$^3$, R$^4$, R$^5$, R$^6$, R$^7$, R$^8$, A and Q have been described above;

b) one or more alumoxanes or compounds able to form an alkylmetallocene cation; and c) optionally an organo aluminum compound.

The process for the polymerization of olefins according to the invention can be carried out in the liquid phase in the presence or absence of an inert hydrocarbon solvent, or in the gas phase. The hydrocarbon solvent can either be aromatic such as toluene, or aliphatic such as propane, hexane, heptane, isobutane or cyclohexane.

The polymerization temperature is generally comprised between −100° C. and +100° C. and, particularly between 10° C. and +90° C. The polymerization pressure is generally comprised between 0.5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

The components of the catalyst can be brought into contact with each other before the polymerization. The pre-contact concentrations are generally between 0.1 and 10$^{-8}$ mol/l for the metallocene component a), while they are generally between 2 and 10$^{-8}$ mol/l for the component b). The pre-contact is generally effected in the presence of a hydrocarbon solvent and, if appropriate, of small quantities of monomer. In the pre-contact it is also possible to use a non-polymerizable olefin such as isobutene, 2-butene and the like.

Further, the molecular weights of the polymer obtained, are distributed over relatively limited ranges. The molecular weight distribution can be represented by the ratio Mw/Mn which, for the present polymers, is generally lower than 4, preferably lower than 3.5 and, more preferably, lower than 3.

The molecular weight distribution can be varied by using mixtures of different metallocene compounds or by carrying out the polymerization in several stages which differ as to the polymerization temperature and/or the concentrations of the molecular weight regulators and/or the monomers concentration. Moreover by carrying out the polymerization process by using a combination of two different metallocene compounds of formula (I) a polymer endowed with a broad melting is produced.

By using the metallocene compounds of formula (I) it is possible to obtain polymers, especially propylene polymers endowed with a higher molecular weight than the polymer obtained in the same conditions with the catalyst of the prior art. In particular the good balance between isotacticity and molecular weight makes the metallocene compounds of formula (I) useful for application on industrial scale.

The process according to the present invention is also suitable for obtaining homo or copolymers of ethylene or higher alpha-olefins such as propylene, 1-butene, 1-pentene, 1-hexene, 4-methyl-1-pentene, 1-octene, 1-decene, 1-dodecene, styrene, 1,5-hexadiene and 1,7-octadiene. Preferred monomers are ethylene, 1-butene or propylene.

The propylene polymers described above are endowed with good balance between optical and mechanical properties.

In the case of propylene copolymers the molar content of propylene derived units is generally higher than 20%, and preferably it is comprised between 50% and 99%. Preferred comonomers are ethylene or 1-butene.

In the case of ethylene copolymers the molar content of ethylene derived units is generally higher than 20%, and preferably it is comprised between 50% and 99%. preferred monomers are propylene, 1-butene, 1-hexene, 1-octene.

The copolymers according to the invention can also contain units derived from polyenes. The content of polyene derived units, if any, is preferably comprised between 0% and 30 mol % and, more preferably between 0% and 20 mol %.

The polyenes that can be used as comonomers in the copolymers according to the present invention are included in the following classes:

non-conjugated diolefins able to cyclopolymerize such as, for example, 1,5-hexadiene, 1-6-heptadiene, 2-methyl-1,5-hexadiene;

dienes capable of giving unsaturated monomeric units, in particular conjugated dienes such as, for example, butadiene and isoprene, and linear non-conjugated dienes, such as, for example, trans 1,4-hexadiene, cis 1,4-hexadiene, 6-methyl-1,5-heptadiene, 3,7-dimethyl-1,6-octadiene, 11-methyl-1,10-dodecadiene, and cyclic non-conjugated dienes such as 5-ethylidene-2-norbornene.

The following examples are given for illustrative purpose and do not intend to limit the invention.

EXAMPLES

General Procedures.

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. $Me_2SiCl_2$ (Aldrich), n-BuLi (Aldrich) and HexLi (Aldrich) were used as received.

The proton spectra of precursors, ligands and metallocenes were obtained on a Bruker DPX 200 spectrometer operating in the Fourier transform mode at room temperature at 200.13 MHz. The samples were dissolved in $CDCl_3$ or $CD_2Cl_2$: $CDCl_3$ (Aldrich, 99.8 atom % D) was stored over molecular sieves (4-5 Å), while $CD_2Cl_2$ (Aldrich, 99.8 atom % D) was used as received. Preparation of the samples was carried out under nitrogen using standard inert atmosphere techniques. The residual peak of $CHCl_3$ or $CHDCl_2$ in the $^1H$ spectra (7.25 ppm and 5.35 ppm, respectively) was used as a reference.

Proton spectra were acquired with a 15° pulse and 2 seconds of delay between pulses; 32 transients were stored for each spectrum.

GC-MS analyses were carried out on a HP 5890—serie 2 gas-chromatograph and a HP 5989B quadrupole mass spectrometer.

Polymer Analysis.

The carbon spectra of the polymers were obtained using a Bruker DPX 400 spectrometer operating in the Fourier transform mode at 120° C. and 100.61 MHz. The samples were dissolved in $C_2D_2Cl_4$. As a reference, the peak of the mmmm pentad in the $^{13}C$ spectra (21.8 ppm) was used.

The carbon spectra were acquired with a 90° pulse and 12 seconds (15 seconds for ethylene based polymers) of delay between pulses and CPD (waltz 16) to remove $^1H$-$^{13}C$ couplings. About 3000 transients were stored for each spectrum.

The intrinsic viscosity (I.V.) was measured in tetrahydronaphthalene (THN) at 135° C.

The melting points and heat of fusion of the polymers ($T_m$) were measured by Differential Scanning Calorimetry (DSC) on a Perkin Elmer DSC-7 instruments, according to the standard method, on 5-10 mg samples sealed into aluminum pans and heated at 200° C. with a heating rate of 10° C./minute. The sample was kept at 200° C. for 2 minutes, then cooled to 25° C. at 10° C./minute, then kept 2 minutes at 25° C., and then heated again up to 200° C. at 10° C./min. The peak temperature of the second melting was assumed as melting temperature ($T_m$) and the area as global melting enthalpy ($\Delta H_f$).

Example 1

Synthesis of dimethylsily{(2-methyl-4-(4-tert-butylphenyl)-1-indenyl)-7-(2,5-dimethyl-cyclopenta[1,2-b:4,3-b']-dithiophene)}zirconium dichloride [C-1]

Synthesis of chloro(2-methyl-4-tert-butylphenyl-1-indenyl)dimethylsilane

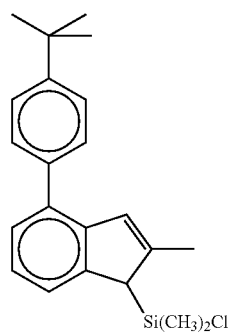

A 2.5 M n-BuLi solution in hexane (4.99 mL, 12.48 mmol, n-BuLi:2-Me-4-(4'-t-BuPh)-1-Ind=1.05:1) was added dropwise at 0° C. to a suspension of 3.12 g of 2-methyl-4-(4'-tert-butylphenyl)-1-indene (MW=262.39, 11.89 mmol) in 20 mL of $Et_2O$. At the end of the addition, the resulting yellow-orange solution was allowed to warm up to room temperature and stirred for 30 min. Then a solution of $Me_2SiCl_2$ (99%, 1.50 mL, d=1.064, MW=129.06, 12.24 mmol, $Me_2SiCl_2$/2-Me-4-(4'-t-BuPh)IndLi=1.02:1) in 10 mL of $Et_2O$ was added at 0° C. to the lithium salt solution, previously cooled to 0° C. The reaction mixture was allowed to warm up to room temperature and stirred for 1 h with final formation of a yellow suspension. The solvents were removed in vacuo and the residue extracted with 50 mL of toluene to remove the LiCl. The filtrate was brought to dryness in vacuo at 40° C. to give an orange oil as product (4.17 g). Yield=83.9%. Punrity (by $^1H$ NMR)=84.9 wt %. About 11% (by $^1H$ NMR) of bis(2-methyl-4-(4'-tert-butylphenyl)-1-indenyl)dimethylsilane was also present as by-product.

$^1H$ NMR (δ, ppm, $CDCl_3$): 0.22 (s, 3H, Si—$CH_3$); 0.47 (s, 3H, Si—$CH_3$); 1.43 (s, 9H, t-Bu); 2.31 (d, 3H, J=0.98 Hz, $CH_3$); 3.69 (s, 1H, CH); 6.88 (s, 1H, Cp-H); 7.17-7.57 (m, 7H, Ar). m/z (%): 356 (40) [M$^+$+2], 355 (31) [M$^+$+1], 354 (100) [M$^+$], 341 (27), 340 (20), 339 (67), 260 (19), 215 (24), 203 (28), 95 (36), 93 (98), 57 (34).

Synthesis of 1-(2-methyl-4-(4'-tert-butylphenylindenyl)-7-(2,5-dimethyl-cyclopenta[1,2-b:4,3-b']-dithiophene)dimethylsilane

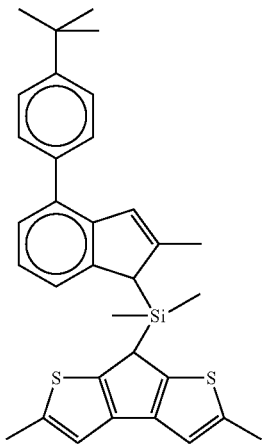

A 2.5 M solution of n-BuLi in hexane (4.11 mL, 10.28 mmol) was added dropwise at 0° C. to a suspension of 2.06 g of 2,5-dimethyl-7H-cyclopenta[1,2-b:4,3-b']-dithiophene (Mw=206.32, 9.98 mmol, n-BuLi: $MeTh_2Cp$=1.03:1) in 25 mL of $Et_2O$. The resulting brown solution was stirred at 0° C. for 30 min and then a solution of 4.17 g of chloro[2-methyl-4-(4'-tert-butylphenyl)-1-indenyl]dimethylsilane (purity by $^1H$ NMR=84.9 wt %, Mw=354.99, 9.97 mmol, 2-Me-4-(4'-t-BuPh)IndSiMe$_2$Cl:MeTh$_2$Cp=1:1) in 15 mL of $Et_2O$ was added at the same temperature. The reaction mixture was then allowed to warm up to room temperature and stirred for 30 min with final formation of a green suspension. The solvents were evaporated under reduced pressure and the residue was extracted with 50 mL of toluene. The extract was dried in vacuo to give 5.82 g of a brown oil, which resulted to be the desired product by $^1$H-NMR spectroscopy (purity by $^1$H-NMR=89.8 wt %, yield=99.8%).

$^1H$ NMR (δ, ppm, $CD_2Cl_2$): −0.30 (s, 3H, Si—$CH_3$); −0.29 (s, 3H, Si—$CH_3$); 1.42 (s, 9H, t-Bu); 2.28 (d, 3H, J=0.98 Hz, $CH_3$); 2.59 (bs, 3H, $CH_3$); 2.61 (bs, 3H, $CH_3$); 3.98 (s, 1H, CH); 4.09 (s, 1H, CH); 6.87 (m, 1H, Cp-H); 6.92 (q, 1H, J=1.17 Hz, CH); 6.94 (q, 1H, J=1.17 Hz, CH); 7.15-7.54 (m, 7H, Ar). m/z (%): 524 (4) [M$^+$], 265 (11), 264 (24), 263 (100), 235 (13), 57 (20).

Synthesis of dimethylsilyl{(2-methyl-4-(4'-tert-butylphenyl)-1-indenyl)-7-(2,5-dimethyl-cyclopental[1,2-b:4,3-b']-dithiophene)}zirconium dichloride

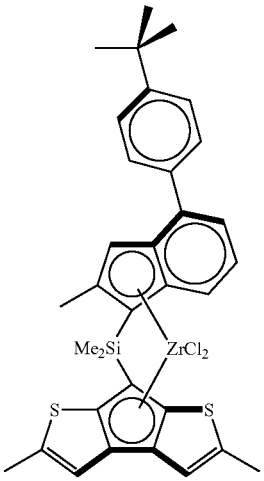

A 2.5 M solution of n-BuLi in hexane (8.16 mL, 20.40 mmol) was added dropwise at 0° C. to a brick red solution of 5.82 g 1-[2-methyl-4-(4'-tert-butylphenyl)indenyl]-7-(2,5-dimethyl-cyclopenta[1,2-b:4,3-b']-dithiophene)dimethylsilane (purity by $^1$H-NMR=89.8 wt %, Mw=524.85, 9.96 mmol, n-BuLi:ligand=2.05:1) in 35 mL of $Et_2O$. The resulting dark brown solution was stirred for 30 min at room temperature and then a suspension of 2.32 g of $ZrCl_4$ (Mw=233.03, 9.96 mmol, $ZrCl_4$:ligand=1:1) in 12 mL of toluene was added at the same temperature. The reaction mixture was stirred at room temperature for 1 h and then the solvents were removed in vacuo. The residue was added of 60 mL of toluene, stirred for 30 min at room temperature and then filtered. The filtrate was eliminated, while the insoluble in toluene was washed with $CH_2Cl_2$ and then dried to give an orange powder as product, which resulted to be the desired catalyst by $^1$H-NMR (5.4 g, yield with LiCl 79.2%).

An aliquot of this powder (1.48 g) was washed very quickly with 10 mL of THF: the residue, an orange powder (0.85 g), contained the target catalyst, while the filtrate (0.63 g) showed partial decomposition to the starting ligand. The orange powder (0.85 g) was subsequently washed with 10 mL of a mixture of isobutanol/toluene ca. 1/1 (v/v) to give, after drying, 0.69 g of the desired catalyst free from LiCl.

The filtrate showed also in this case partial decomposition to the starting ligand.

$^1$H NMR (δ, ppm, CDCl$_3$): 1.16 (s, 3H, Si—CH$_3$); 1.32 (s, 12H, t-Bu and Si—CH$_3$); 2.34 (bs, 3H, CH$_3$); 2.41 (bs, 3H, CH$_3$); 2.59 (bs, 3H, CH$_3$); 6.62 (bs, 1H, CH); 6.75 (bs, 1H, CH); 6.87-7.65 (m, 8H, Cp-H and Ar).

Example 2

Synthesis of dimethylsilyl{(2-methyl-4-(3',5'-di-tert-butylphenyl)-1-indenyl)-7-(2,5-dimethyl-cyclopental[1,2-b:4,3-b']-dithiophene)}zirconium dichloride [C-2]

Synthesis of 1-(2-methyl-4-(3',5'-di-tert-butylphenylindenyl)-7-(2,5-dimethyl-cyclopental[1,2-b:4,3-b']-dithiophene)dimethylsilane

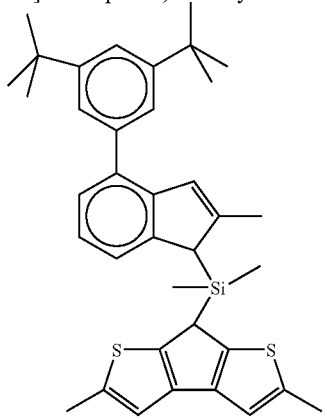

A 2.3 M HexilLithium(HexLi) solution in hexane (6.40 mL, 14.72 mmol) was added dropwise at 0° C. to a suspension of 2.90 g of 2,5-dimethyl-7H-cyclopenta[1,2-b:4,3-b']-dithiophene (Mw=206.32, 14.06 mmol, HexLi:MeTh$_2$Cp=1.05:1) in 25 mL of Et$_2$O. The resulting brown solution was stirred at 0° C. for 1 h and then a solution of 5.76 g of chloro[2-methyl-4-(3',5'-di-tert-butylphenyl)-1-indenyl]dimethylsilane (J. Schulte sample, Mw=411.11, 14.01 mmol, 2-Me-4-(3',5'-di-t-BuPh)IndSiMe$_2$Cl:MeTh$_2$Cp=1:1) in 20 mL of Et$_2$O was added at the same temperature. Because of the low solubility of the product in the ether/hexane mixture, 5 mL of THF were added. The reaction mixture was then allowed to warm up to room temperature and stirred for 16 h with final formation of a brown suspension. The solvents were evaporated under reduced pressure and the residue was extracted with 20 mL of toluene. The extract was dried in vacuo to give 7.66 g of an orange sticky solid, which resulted to be the desired product by $^1$H-NMR spectroscopy (yield=94.1%, purity ca. 90% wt). The ligand was used as such in the next step without further purification.

$^1$H NMR (δ, ppm, CD$_2$Cl$_2$): −0.24 (s, 3H, Si—CH$_3$); −0.26 (s, 3H, Si—CH$_3$); 1.45 (s, 18H, t-Bu); 2.30 (s, 3H, CH$_3$); 2.60 (bs, 3H, CH$_3$); 2.62 (bs, 3H, CH$_3$); 4.00 (bs, 1H, CH); 4.06 (bs, 1H, CH); 6.86 (bs, 1H, Cp-H); 6.94 (q, 1H, J=1.17 Hz, CH); 6.95 (q, 1H, J=1.17 Hz, CH); 6.95 (q, 1H, J=1.17 Hz, CH); 7.18-7.50 (m, 6H, Ar). m/z (%): 581 (1) [M$^+$+1], 376 (25), 319 (14), 265 (14), 264 (22), 263 (100), 248 (12), 235 (22), 205 (10), 57 (84), 41 (17).

Synthesis of dimethylsilyl{(2-methyl-4-(3',5'-di-tert-butylphenyl)-1-indenyl)-7-(2,5-dimethyl-cyclopental[1,2-b:4,3-b']-dithiophene)}zirconium dichloride [C-2]

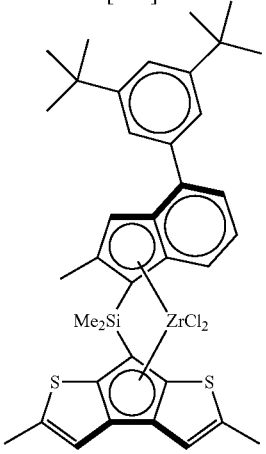

A 2.3 M HexLi solution (4.61 mL, 10.60 mmol) was added dropwise at 0° C. to a solution of 3.00 g of 1-[2-methyl-4-(3',5'-di-tert-butylphenyl)indenyl]-7-(2,5-dimethyl-cyclopenta[1,2-b:4,3-b']-dithiophene)dimethylsilane (Mw=580.96, 5.16 mmol, HexLi:ligand=2.05:1) in 30 mL of Et$_2$O. At the end of the addition, the resulting brown solution was stirred for 2 h at room temperature with final formation of a light brown suspension. Subsequently a suspension of 1.20 g of ZrCl$_4$ (Mw=233.03, 5.15 mmol, ZrCl$_4$:ligand=1:1) in 20 mL of toluene was added at 0° C. The reaction mixture was then allowed to warm up to room temperature and stirred for 16 h. The solvents were removed in vacuo and the crude residue was extracted with 75 mL of toluene. The extract was treated with 55 mL of a mixture of isobutanol/toluene ca. 1/10 (v/v), stirred for 15 min at room temperature and then filtered. The filtrate was eliminated, while the insoluble in isobutanol/toluene was dried to give 2.20 g of an orange powder, which resulted to be by $^1$H-NMR analysis the desired complex free from LiCl (isolated yield=57.6%).

$^1$H NMR (δ, ppm, CD$_2$Cl$_2$): 1.21 (s, 3H, Si—CH$_3$); 1.36 (s, 18H, t-Bu); 1.38 (s, 3H, Si—CH$_3$); 2.38 (s, 3H, CH$_3$); 2.46 (d, 3H, J=1.17 Hz, CH$_3$); 2.64 (d, 3H, J=1.17 Hz, CH$_3$); 6.71 (q, 1H, J=1.17 Hz, CH); 6.86 (q, 1H, J=1.17 Hz, CH); 6.87 (bs, 1H, Cp-H); 6.93-7.73 (m, 6H, Ar).

Example 3

Synthesis of dimethylsilyl{(2-ethyl-4-(4'-tert-butylphenyl)-1-indenyl)-7-(2,5-dimethyl-cyclopental[1,2-b:4,3-b']-dithiophene)}zirconium dichloride [C-3]

Synthesis of chloro(2-ethyl-4'-tert-butylphenyl-1-indenyl)dimethylsilane

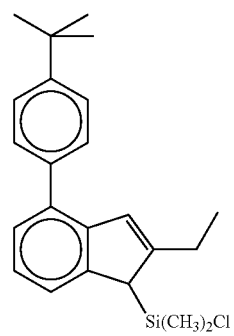

A 2.3 M HexLi (hexylithium) solution in hexane (8.30 mL, 19.09 mmol, HexLi:2-Et-4-(4'-t-BuPh)-1-Ind=1.06:1) was added dropwise at 0° C. to a solution of 5.0 g of 2-ethyl-4-(4'-tert-butylphenyl)-1-indene (MW=276.42, 18.09 mmol) in 50 mL of Et$_2$O. At the end of the addition, the resulting orange solution was allowed to warm up to room temperature and stirred for 1 h. An aliquot of this solution was quenched with CD$_3$OD and dried: the related $^1$H NMR analysis in CD$_2$Cl$_2$ showed complete conversion of the starting indene to the corresponding lithium salt. A solution of Me$_2$SiCl$_2$ (99%, 2.20 mL, d=1.064, MW=129.06, 17.96 mmol, Me$_2$SiCl$_2$/2-Et-4-(4'-t-BuPh)In-dLi=1:1) in 10 mL of Et$_2$O was added at 0° C. to the lithium salt solution, previously cooled to 0° C. too. The reaction mixture was allowed to warm up to room temperature and stirred for 1 h and 30 min with final formation of a light yellow suspension. The solvents were removed in vacuo and the residue extracted with 50 mL of toluene to remove the LiCl. The filtrate was brought to dryness in vacuo at 40° C. to give a sticky orange solid as product (6.60 g). Yield=99.6%.

$^1$NMR (δ, ppm, CD$_2$Cl$_2$): 0.27 (s, 3H, Si—CH$_3$); 0.48 (s, 3H, Si—CH$_3$); 1.29 (t, 3H, J=7.58 Hz, CH$_3$); 1.45 (s, 9H, t-Bu); 2.54-2.88 (m, 2H, CH$_2$); 3.83 (s, 1H, CH); 6.92 (s, 1H, Cp-H); 7.20-7.59 (m, 7H, Ar). m/z (%): 370 (22) [M$^+$+2], 369 (18) [M$^+$+1], 368 (55) [M$^+$], 355 (11), 353 (27), 275 (17), 274 (23), 219 (14), 217 (14), 215 (17), 202 (18), 95 (36), 93 (100), 57 (47), 41 (14).

Synthesis of 1-(2-ethyl-4-(4'-tert-butylphenylinde-nyl)-7-(2,5-dimethyl-cyclopenta[1,2-b:4,3-b']-dithiophene)dimethylsilane

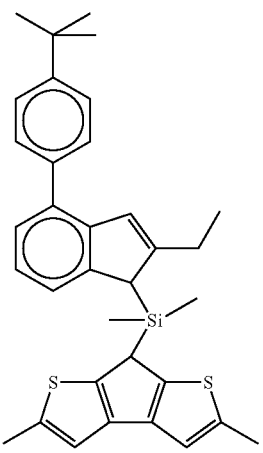

A 2.3 M HexLi solution in hexane (4.40 mL, 10.12 mmol) was added dropwise at 0° C. to a suspension of 2.07 g of 2,5-dimethyl-7H-cyclopenta[1,2-b:4,3-b']-dithiophene (Mw=206.32, 10.03 mmol, HexLi: MeTh$_2$Cp=1.01:1) in 30 mL of Et$_2$O. The resulting brown solution was stirred at 0° C. for 1 h and then a solution of 3.71 g of chloro[2-ethyl-4-(4'-tert-butylphenyl)-1-indenyl]dimethylsilane (Mw=369.02, 10.05 mmol, 2-Et-4-(4'-t-BuPh)IndSiMe$_2$Cl: MeTh$_2$Cp=1:1) in 25 mL of Et$_2$O was added at the same temperature. The reaction mixture was then allowed to warm up to room temperature and stirred for 16 h with final formation of a green-brown suspension. The solvents were evaporated under reduced pressure and the residue was extracted with 40 mL of toluene. The extract was dried in vacuo to give 5.70 g of a brown sticky solid, which resulted to be the desired product by $^1$H-NMR spectroscopy (purity by $^1$H-NMR=91.3 wt %, isolated yield=96.3%). About 8.7 wt % of starting 2,5-dimethyl-7H-cyclopenta[1,2-b:4,3-b']-dithiophene was also present.

$^1$H NMR (δ, ppm, CD$_2$Cl$_2$): −0.29 (s, 3H, Si—CH$_3$); −0.30 (s, 3H, Si—CH$_3$); 1.26 (t, 3H, J=7.58 Hz, CH$_3$); 1.44 (s, 9H, t-Bu); 2.44-2.75 (m, 2H, CH$_2$); 2.59 (bs, 3H, CH$_3$); 2.61 (bs, 3H, CH$_3$); 4.07 (bs, 2H, CH); 6.90 (s, 1H, Cp-H); 6.92 (q, 1H, J=1.17 Hz, CH); 6.94 (q, 1H, J=1.17 Hz, CH); 7.06-7.56 (m, 7H, Ar).

Synthesis of dimethylsilyl{(2-ethyl-4-(4'-tert-bu-tylphenyl)-1-indenyl)-7-(2,5-dimethyl-cyclopenta[1, 2-b:4,3-b']-dithiophene)}zirconium dichloride [C-3]

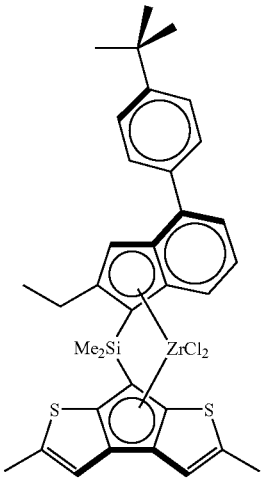

A 2.3 M HexLi solution (4.61 mL, 10.60 mmol) was added dropwise at 0° C. to a solution of 2.86 g of 1-[2-ethyl-4-(4'-tert-butylphenyl)indenyl]-7-(2,5-dimethyl-cy-clopenta[1,2-b:4,3-b']-dithiophene)dimethylsilane (Mw=538.88, 5.31 mmol, HexLi:ligand=2:1) in 30 mL of Et$_2$O. The resulting brown solution was allowed to warm up to room temperature and stirred for 2 h. Then a suspension of 1.24 g of ZrCl$_4$ (Mw=233.03, 5.32 mmol, ZrCl$_4$:ligand=1: 1) in 30 mL of toluene was added. The reaction mixture was stirred at room temperature for 1 h and then the solvents were removed in vacuo. The residue was treated with 50 mL of a mixture of isobutanol/toluene ca. 1/3 (v/v), stirred for 10 min at room temperature and then filtered. The filtrate was eliminated, while the insoluble in isobutanol/toluene was dried to give 1.75 g of an orange powder, which resulted to be by $^1$H-NMR analysis the desired catalyst free from LiCl (isolated yield=46.9%).

$^1$H NMR (δ, ppm, CD$_2$Cl$_2$): 0.11 (s, 6H, Si—CH$_3$); 1.17 (t, 3H, J=7.34 Hz, CH$_3$); 1.38 (s, 9H, t-Bu); 2.46 (d, 3H, J=1.17 Hz, CH$_3$); 2.62 (d, 3H, J=1.17 Hz, CH$_3$); 2.53-2.94 (m, 2H, CH$_2$); 6.68 (q, 1H, J=1.17 Hz, CH); 6.82 (q, 1H, J=1.17 Hz, CH); 6.92-7.74 (m, 8H, Cp-H and Ar).

Comparative Example 4
Synthesis of dimethylsilyl{(2-methyl-4-phenyl-1-indenyl)-7-(2,5-dimethyl-cyclopenta[1,2-b:4,3-b']-dithiophene)}zirconium dichloride [C-4]
Synthesis of chloro(2-methyl-4-phenyl-1-indenyl)dimethylsilane

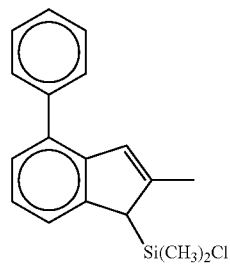

A 2.5 M solution of n-BuLi in hexane (4.85 mL, 12.12 mmol) was added at 0° C. to a solution of 2.50 g of 2-methyl-4-phenyl-indene (Boulder Scientific Company, Mw=206.29, 12.12 mmol, n-BuLi:2-Me-4-Ph-Ind=1:1) in 30 mL of ether. The resulting mixture was stirred for additional 2 h at room temperature with final formation of an orange solution. This solution was cooled again to 0° C. and added slowly of a solution of 1.58 mL of dichlorodimethylsilane (Aldrich, Mw=129.06, d=1.064, 13.03 mmol, Me$_2$SiCl$_2$:2-Me-4-Ph-Ind=1.08:1) in 20 mL of ether. The reaction mixture was then allowed to warm up to room temperature and stirred for 1 h. The final straw yellow suspension was concentrated under vacuum and the residue was extracted with 50 mL of toluene. The extract was dried under vacuum to give 3.36 g of a straw yellow solid, which was characterized by GC-MS analysis and $^1$H-NMR spectroscopy. Yield=92.8%.

$^1$H NMR (δ, ppm, CDCl$_3$): 0.24 (s, 3H, Si—CH$_3$); 0.48 (s, 3H, Si—CH$_3$); 2.31 (d, 3H, CH$_3$, J=0.78 Hz); 3.70 (bs, 1H, CH); 6.85 (m, 1H, CH, J=0.78 Hz); 7.19-7.59 (m, 8H, Ar). m/z (%): 300 (26) [M$^+$+2], 299 (18) [M$^+$+1], 298 (72) [M$^+$], 205 (23), 204 (45), 203 (28), 202 (32), 189 (15), 165 (13), 95 (35), 93 (100).

Synthesis of (2-methyl-4-phenyl-1-indenyl)-7-(2,5-dimethyl-cyclopenta[1,2-b:4,3-b']-dithiophene)dimethylsilane

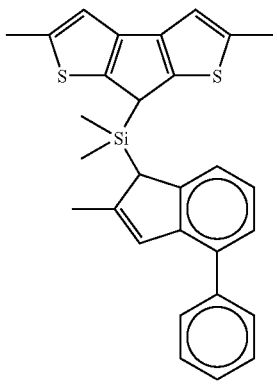

A 2.5 M solution of n-BuLi in hexane (2.72 mL, 6.80 mmol) was added at −20° C. to a solution of 1.40 g of 2,5-dimethyl-7H-cyclopenta[1,2-b:4,3-b']-dithiophene (Mw=206.32, 90.7%, 6.15 mmol, n-BuLi:MeTh$_2$Cp=1.1:1) in 30 mL of ether. The resulting mixture was stirred for additional 1 h at 0° C. with final formation of a dark brown suspension. This suspension was cooled again to −20° C. and added slowly of a solution of 1.90 g of chloro(2-methyl-4-phenyl-1-indenyl)dimethylsilane (Mw=298.89, 6.37 mmol, (2-Me-4-Ph-1-Ind)SiMe$_2$Cl:MeTh$_2$Cp=1.04:1) in 20 mL of ether. The reaction mixture was then allowed to warm up to room temperature and stirred for 2 h. The final dark solution (almost black) was concentrated under vacuum and the residue extracted with 50 mL of toluene to give an oily product, which was treated at 30° C. under stirring with 30 mL of pentane. After 15 min stirring a powdery solid was formed and isolated by filtration. After drying in vacuo, 2.03 g of a brown product was recovered.

Purity (by GC-MS)=83.8%. Yield of the pure product=59.0%. $^1$H NMR (δ, ppm, CDCl$_3$): −0.35 (s, 3H, Si—CH$_3$); −0.32 (s, 3H, Si—CH$_3$); 2.23 (d, 3H, CH$_3$, J=0.78 Hz); 2.55 (bs, 3H, CH$_3$); 2.58 (bs, 3H, CH$_3$); 3.96 (s, 1H, CH); 4.04 (s, 1H, CH); 6.82 (q, 1H, CH, J=0.78 Hz); 6.86 (q, 1H, CH, J=1.17 Hz); 6.88 (q, 1H, CH, J=1.17 Hz); 7.13-7.59 (m, 8H, Ar). m/z (%): 469 (10) [M$^+$+1], 468 (24) [M$^+$], 264 (28), 263 (100), 248 (14), 247 (21), 235 (20), 205 (13), 203 (16), 190 (10), 59 (14).

Synthesis of dimethylsilyl{(2-methyl-4-phenyl-1-indenyl)-7-(2,5-dimethyl-cyclopenta[1,2-b:4,3-b']-dithiophene)}zirconium dichloride [C-4]

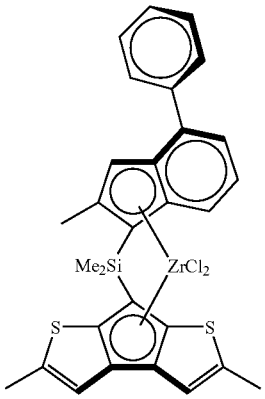

A solution of 2.58 g (5.5 mmol) of (2-methyl-4-phenyl-1-indenyl)-7-(2,5-dimethyl-cyclopenta[1,2-b:4,3-b']-dithiophene)dimethylsilane in 40 mL of ether was treated at −70° C. with 7.0 mL of a 1.6 M n-BuLi solution (11.2 mmol). The reaction mixture was allowed to reach room temperature and stirred for 1 h. The solvent was removed under reduced pressure and the dilithium salt obtained was suspended in hexane. After cooling to −70° C., 1.28 g (5.5 mmol) of ZrCl$_4$ were added. The reaction mixture was stirred at room temperature overnight, the yellow precipitate was filtered, washed twice with ether, dried and finally recrystallized from CH$_2$Cl$_2$. Yield 1.65 g (48%). The title compound was characterized by $^1$H NMR spectroscopy.

Example 5

Synthesis of dimethylsilanediyl{(1-(2-methyl-4-naphthylindenyl)-7-(2,5dimethyl-cyclopenta[1,2-b:4,3-b']-dithiophene)}zirconium dichloride [C-5]

Synthesis of chloro(2-methyl-4-naphthyl-1-indenyl)dimethylsilane

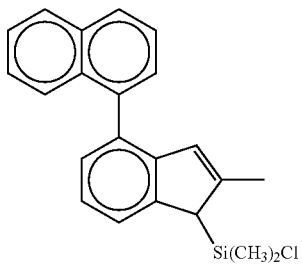

A 1.5 M MeLi solution in Et$_2$O (9.90 mL, 14.85 mmol, MeLi:2-Me-4-naphthyl-1-indene=1:1) was added dropwise at 0° C. to a solution of 3.88 g of 2-methyl-4-naphthylindene (MW=256.35, 98%, 14.83 mmol) in 45 mL of Et$_2$O. At the end of the addition a light yellow suspension was obtained.

The latter was kept at 0° C. for 15 min and then allowed to warm up to room temperature. After 1 h stirring an aliquot of the suspension was taken, treated with D$_2$O and dried: its $^1$H NMR analysis in CD$_2$Cl$_2$ showed complete conversion of 2-methyl-4-naphthylindene to a 70:30 mixture of 1-deuterium-2-methyl-4-naphthyl-1-indene and 1-deuterium-2-methyl-7-naphthyl-1-indene (see below $^1$H NMR analysis). The expected lithium salt was quantitatively obtained. It was then added at 0° C. to a solution of Me$_2$SiCl$_2$ (98%, 1.96 g, d=1.064, MW=129.06, 14.88 mmol, Me$_2$SiCl$_2$/2-Me-4-naphthyl-1-IndLi=1:1) in 30 mL of Et$_2$O, previously cooled to 0° C. too. The reaction mixture was allowed to warm up to room temperature and stirred for 20 h with final formation of a white suspension. After this time a $^1$H NMR analysis showed complete conversion of the starting material. The solvents were removed in vacuo and the residue was extracted with 50 mL of toluene to remove the LiCl. The light yellow filtrate was brought to dryness in vacuo at 40° C. to give a light yellow solid as product, which was analysed by NMR spectroscopy (5.28 g). The latter showed the presence of the desired product as a mixture of two diastereoisomers in ratio of 1 (1):1.4 (2), probably due to a blocked rotation around the C4-naphthyl bond. Crude yield=100%. The product was used as such in the next step without further purification.

$^1$H NMR (δ, ppm, CD$_2$Cl$_2$): 0.28 (s, 3H, Si—CH$_3$, 1); 0.35 (s, 3H, Si—CH$_3$, 2); 0.48 (s, 3H, Si—CH$_3$, 1); 0.53 (s, 3H, Si—CH$_3$, 2); 2.20 (m, 3H, J=0.78 Hz, CH$_3$, 2); 2.22 (m, 3H, J=0.78 Hz, CH$_3$, 1); 3.76 (s, 1H, CH, 2); 3.77 (s, 1H, CH, 1); 6.18 (m, 1H, Cp-H, 2); 6.28 (m, 1H, Cp-H, 1); 7.26-7.98 (m, 20H, Ar, 1 and 2). NOESY (CD$_2$Cl$_2$) δ$^1$H/δ$^1$H=0.28, 0.48/3.77 (Si—CH$_3$/CH, 1); 0.35, 0.53/3.76 (Si—CH$_3$/CH, 2); 2.22/3.77 (CH$_3$/CH, 1); 2.20/3.76 (CH$_3$/CH, 2); 2.22/6.28 (CH$_3$/Cp-H, 1); 2.20/6.18 (CH$_3$/Cp-H, 2); 6.28/7.59-7.80 (Cp-H/H7, 1); 6.18/7.59-7.80 (Cp-H/H7, 2). COSY (CD$_2$Cl$_2$) δ$^1$/δ$^1$H=2.22/3.77 (CH$_3$/CH, 1); 2.20/3.76 (CH$_3$/CH, 2); 2.22/6.28 (CH$_3$/Cp-H, 1); 2.20/6.18 (CH$_3$/Cp-H, 2).

Synthesis of 1-(2-methyl-4-naphthylindenyl)-7-(2,5-dimethyl-cyclopenta[1,2-b:4,3-b']-dithiophene)dimethylsilane

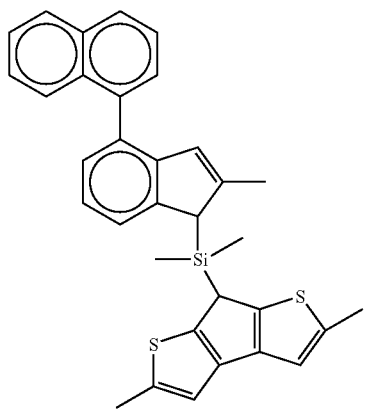

A 2.5 M solution of n-BuLi in hexane (5.40 mL, 13.50 mmol) was added dropwise at 0° C. under stirring to a suspension of 2.81 g of 2,5-dimethyl-7H-cyclopenta[1,2-b:4,3-b']-dithiophene (99%, Mw=206.32, 13.48 mmol, n-BuLi: MeTh$_2$Cp=1.00: 1) in 40 mL of Et$_2$O in a 100 mL Schlenk flask. The resulting dark brown suspension was stirred at 0° C. for 1 h, then cooled to −20° C. and added slowly to a solution of 4.71 g of chloro(2-methyl-4-naphthyl-1-indenyl)dimethylsilane (Mw=348.95, 13.50 mmol, 2-Me-4-naphthyl-IndSiMe$_2$Cl:MeTh$_2$Cp=1:1) in 30 mL of Et$_2$O, previously cooled to −20° C. too. The reaction mixture was kept for 15 min at −20° C. and then allowed to warm up to room temperature and stirred for 2 h. CH$_3$OH (1 mL) was added and the suspension turned from brown to yellow. The solvents were removed in vacuo and the residue was extracted with 50 mL of toluene to give 6.64 g of a pitch-brown solid. Since its $^1$H NMR analysis in CD$_2$Cl$_2$ showed the presence of unwelcome by-products, the solid was washed first with pentane and then with Et$_2$O yielding after drying 2.01 g of a white powder, which was analysed by NMR spectroscopy and GC-MS analysis. The product resulted a mixture of two diastereoisomers in ratio of ca. 1 (1):1.4 (2), probably due to a blocked rotation around the C4-naphthyl bond. Isolated yield 28.7%. Purity 97.3% by GC-MS. Bis(2-methyl-4-naphthyl-1-indenyl)dimethylsilane was present in 1.1% wt. by GC-MS.

$^1$H NMR (δ, ppm, CD$_2$Cl$_2$): −0.25 (s, 3H, Si—CH$_3$, 1); −0.22 (s, 3H, Si—CH$_3$, 2); −0.21 (s, 3H, Si—CH$_3$, 1); −0.16 (s, 3H, Si—CH$_3$, 2); 2.21 (d, 3H, J=0.98 Hz, CH$_3$, 2); 2.23 (D, 3H, J=0.98 Hz, CH$_3$, 1); 2.64 (m, 6H, CH$_3$, 1 and 2); 2.66 (m, 6H, CH$_3$, 2 and 1); 4.10 (S, 2H, CH, H1, 1 and 2); 4.16 (s, 1H, CH, 1); 4.22 (s, 1H, CH, 2); 6.26 (m, 1H, Cp-H, 2); 6.36 (m, 1H, Cp-H, 1); 6.97-7.01 (m, 4H, CH, 1 and 2); 7.27-8.03 (m, 20H, Ar, 1 and 2). NOESY (CD$_2$Cl$_2$) δ$^1$H/δ$^1$H=−0.25/2.23 (Si—CH$_3$/CH$_3$, 1); −0.22/2.21 (Si—CH$_3$/CH$_3$, 2); −0.25, −0.22, −0.21, −0.16/4.10 (Si—CH$_3$/CH, H1, 1 and 2); −0.25, −0.21/4.16 (Si—CH$_3$/CH, 1); −0.22, −0.16/4.22 (Si—CH$_3$/CH, 2); 2.21, 2.23/4.10 (CH$_3$/CH, H1, 1 and 2); 2.23/4.16 (CH$_3$/CH, 1); 2.21/4.22 (CH$_3$/CH, 2); 2.64, 2.66/6.97-7.01 (CH$_3$/CH, 1 and 2). COSY (CD$_2$Cl$_2$) δ$^1$H/δ$^1$H=2.21, 2.23/4.10 (CH$_3$/CH, H1, 1 and 2); 2.23/6.36 (CH$_3$/Cp-H, 1); 2.21/6.26 (CH$_3$/Cp-H, 2); 2.64, 2.66/4.16 (CH$_3$/CH, 1); 2.64, 2.66/4.22 (CH$_3$/CH, 2); 4.10/6.26, 6.36 (CH, H1/Cp-H, 1 and 2); 4.16/6.97-7.01 (CH/CH, 1); 4.22/6.97-7.01 (CH/CH, 2). $^{13}$C NMR (δ, ppm, CD$_2$Cl$_2$): −8.04 (Si—CH$_3$, 1C, 2); −7.92 (Si—CH$_3$, 1C, 1); −7.54 (Si—CH$_3$, 1C, 2); −7.46 (Si—CH$_3$, 1C, 1); 16.26 (CH$_3$ in MeTh$_2$Cp, 4C, 1 and 2); 17.92 (CH$_3$ in 2, 2C, 1 and 2); 39.77 (CH in MeTh$_2$Cp, 1C, 1); 39.87 (CH in MeTh$_2$Cp, 1C, 2); 47.43 (CH, 1C, 1); 47.46 (CH, 1C, 2); 116.82 (CH in MeTh$_2$Cp, 2C, 1); 116.91 (CH in MeTh$_2$Cp, 2C, 2); 126.82 (Cp-H, 1C, 1); 126.91 (Cp-H, 1C, 2); 122.63-128.56 (Ar, 20 CH, 1 and 2); 132.39-147.86 (Ar, 20 C, 1 and 2). The peaks were assigned by a DEPT experiment. m/z (%): 519 (19) [M$^+$+1], 518 (43) [M$^+$], 314 (29), 313 (100), 297 (14), 264 (18), 263 (88), 235 (16), 204 (13), 203 (15).

Synthesis of dimethylsilanediyl{(1-(2-methyl-4-naphthylindenyl)-7-(2,5-dimethyl-cyclopenta[1,2-b:4,3-b']-dithiophene)}zirconium dichloride [C-5]

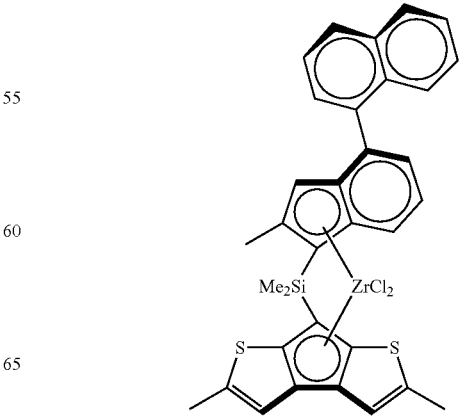

A 2.5 M solution of n-BuLi in hexane (3.40 mL, 8.50 mmol) was added dropwise at 0° C. under stirring to a yellow-brown suspension of 2.16 g of 1-(2-methyl-4-naphthylindenyl)-7-(2,5-dimethyl-cyclopenta[1,2-b:4,3-b']-dithiophene)dimethylsilane (Mw=518.81, 4.16 mmol, n-BuLi:ligand=2.04:1) in 40 mL of Et$_2$O. The resulting brown solution was allowed to warm up slowly to room temperature and stirred for 1 h. Then it was cooled to 0° C. to add slowly a suspension of 0.97 g of ZrCl$_4$ (Mw=233.03, 4.16 mmol, ZrCl$_4$:ligand=1:1) in 20 mL of toluene, previously cooled to 0° C. too. The reaction mixture was stirred at room temperature for 2 h with final formation of a dark orange-red suspension. The solvents were removed in vacuo and the obtained red-brown solid was treated at room temperature with 30 mL of a 1/5 (v/v) isobutanol/toluene mixture. After 15 min stirring the suspension was filtered on a G3 frit: the filtrate was discarded, while the residue was dried at room temperature in vacuo for 8 h to give an orange powder as product (1.41 g, free from LiCl). Isolated yield 49.9%.

$^1$H NMR (δ, ppm, CDCl$_3$): 1.22 (s, 3H, Si—CH$_3$); 1.42 (s, 3H, Si—CH$_3$); 2.32 (s, 3H, CH$_3$ in 2); 2.51 (s, 3H, CH$_3$ in Me$_2$ThCp); 2.61 (s, 3H, CH$_3$ in Me$_2$ThCp); 6.45 (s, 1H, Cp-H); 6.70 (s, 1H, CH); 6.79 (s, 1H, CH); 7.00-7.95 (m, 10H, Ar).

Polymerization Examples 6-12 and Comparative Examples 13-14

The cocatalyst methylalumoxane (MAO) was a commercial product which was used as received (Witco AG, 10% wt/vol toluene solution, 1.7 M in Al). The catalyst mixture was prepared by dissolving the desired amount of the metallocene with the proper amount of the MAO solution, (Al/Zr ratio=500) obtaining a solution which was stirred for 10 min at ambient temperature before being injected into the autoclave.

Polymerization (General Procedure)

2 mmol of Al(i-Bu)$_3$ (as a 1M solution in hexane) and 600 g of propylene were charged at room temperature in a 2.5-L jacketed stainless-steel autoclave, equipped with magnetically driven stirrer and a 35-mL stainless-steel vial, connected to a thermostat for temperature control, previously purified by washing with an Al(i-Bu)$_3$ solution in hexanes and dried at 50° C. in a stream of propene. The autoclave was then thermostatted at the polymerization temperature (Tp), and then the toluene solution containing the catalyst/cocatalyst mixture was injected in the autoclave by means of nitrogen pressure through the stainless-steel vial, and the polymerization carried out at constant temperature for 1 hour. The polymerization was stopped by pressurizing CO into the reactor. After venting the unreacted monomer and cooling the reactor to room temperature, the polymer was dried under reduced pressure at 60° C.

The polymerization conditions and the characterization data of the obtained polymers are reported in Table 1

TABLE 1

| Metallocene | | | | Activity | I.V. | Tm | |
|---|---|---|---|---|---|---|---|
| Ex. | Type | mg | Tp ° C. | (kg/(g$_{cat}$ × h)) | (dL/g) | (° C.) | mm % |
| 6 | C-1 | 0.5 | 60 | 140 | 1.5 | 147 | 94.6 |
| 7 | C-1 | 0.5 | 70 | 240 | 1.1 | 145 | 94.2 |
| 8 | C-2 | 0.5 | 60 | 60 | 1.9 | 150 | n.a. |
| 9 | C-2 | 0.5 | 70 | 80 | 1.4 | 145 | n.a. |
| 10 | C-3 | 0.5. | 60 | 120 | 1.5 | 150 | n.a. |
| 11 | C-3 | 0.5 | 70 | 224 | 1.1 | 147 | n.a. |
| 12 | C-5 | 0.5 | 70 | 60 | 1.2 | 156 | n.a. |

TABLE 1-continued

| Metallocene | | | | Activity | I.V. | Tm | |
|---|---|---|---|---|---|---|---|
| Ex. | Type | mg | Tp ° C. | (kg/(g$_{cat}$ × h)) | (dL/g) | (° C.) | mm % |
| 13* | C-4 | 1 | 60 | 100 | 1.3 | 146 | 94.1 |
| 14* | C-4 | 0.5 | 70 | 126 | 1.0 | 143 | 93.9 |

*comparative
n.a. = not available

The invention claimed is:

1. A metallocene compound of formula (I):

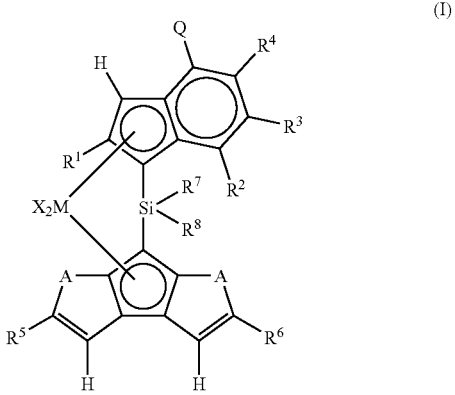

wherein:
M is selected from the group consisting of zirconium, titanium and hafnium;

X, same or different, is a hydrogen atom, a halogen atom, a R, OR, OR'O, OSO$_2$CF$_3$, OCOR, SR, NR$_2$ or PR$_2$ group, wherein the R substituents are linear or branched, saturated or unsaturated C$_1$-C$_{20}$-alkyl, C$_3$-C$_{20}$-cycloalkyl, C$_6$-C$_{20}$-aryl, C$_7$-C$_{20}$-alkylaryl, C$_7$-C$_{20}$-arylalkyl radicals, optionally containing one or more heteroatoms belonging to groups 13-17 of the Periodic Table of the Elements and the R' substituent is a divalent radical selected from the group consisting of C$_1$-C$_{20}$-alkylidene, C$_6$-C$_{20}$-arylidene, C$_7$-C$_{20}$-alkylarylidene, and C$_7$-C$_{20}$-arylalkylidene;

R$^1$ is a linear C$_1$-C$_{20}$-alkyl radical;

R$^2$ is a hydrogen atom or a linear or branched, saturated or unsaturated C$_1$-C$_{20}$-alkyl radical;

R$^3$ and R$^4$, same or different, are hydrogen atoms or a linear or branched, saturated or unsaturated C$_1$-C$_{20}$-alkyl, C$_3$-C$_{20}$-cycloalkyl, C$_6$-C$_{20}$-aryl, C$_7$-C$_{20}$-alkylaryl, C$_7$-C$_{20}$-arylalkyl radicals, optionally containing one or more heteroatoms belonging to groups 13-17 of the Periodic Table of the Elements; or they can form together a condensed saturated or unsaturated 5 or 6 membered ring, optionally containing one or more heteroatoms belonging to groups 13-16 of the Periodic Table of the Elements, said ring optionally bearing one or more substituents;

R$^5$ and R$^6$, same or different, are hydrogen atoms or a linear or branched, saturated or unsaturated C$_1$-C$_{20}$-alkyl, C$_3$-C$_{20}$-cycloalkyl, C$_6$-C$_{20}$-aryl, C$_7$-C$_{20}$-alkylaryl, C$_7$-C$_{20}$-arylalkyl radicals, optionally containing one or more heteroatoms belonging to groups 13-17 of the Periodic Table of the Elements; R$^7$ and R$^8$, same or different, are hydrogen atoms or a linear or branched, saturated or unsaturated C$_1$-C$_{20}$-alkyl, C$_3$-C$_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements;

A, same or different, is a sulphur (S) atom or an oxygen (O) atom;

Q is a radical of formula (II), (III) or (IV)) being bonded to the indenyl at the position marked with the symbol *;

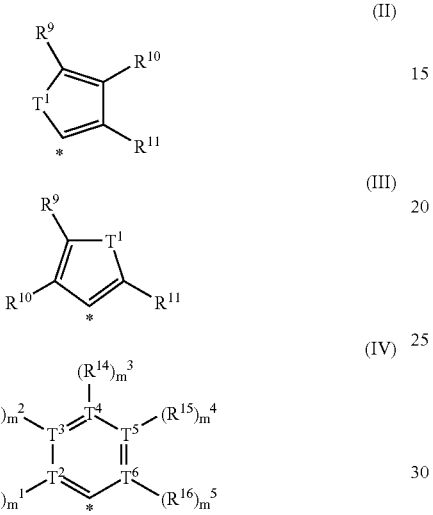

wherein:

$T^1$ is a sulphur (S) atom, an oxygen (O) atom or a NR group, R being defined as above;

$R^9$, $R^{10}$ and $R^{11}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or $R^9$ and $R^{10}$ can form together a condensed saturated or unsaturated 5 or 6 membered ring, optionally containing one or more heteroatoms belonging to groups 13-16 of the Periodic Table of the Elements, said ring optionally bearing one or more substituents;

$T^2$, $T^3$, $T^4$, $T^5$ and $T^6$, same or different, are carbon atoms (C) or nitrogen atoms (N);

each of $m^1$, $m^2$, $m^3$, $m^4$ and $m^5$ is 0 when the correspondent $T^2$, $T^3$, $T^4$, $T^5$ and $T^6$ is a nitrogen atom and is 1 when the correspondent $T^2$, $T^3$, $T^4$, $T^5$ and $T^6$ is a carbon atom;

$R^{12}$, $R^{13}$, $R^{14}$, $R^{15}$ and $R^{16}$ same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or two vicinal $R^{12}$, $R^{13}$, $R^{14}$, $R^{15}$ can form together a condensed saturated or unsaturated 5 or 6 membered ring, optionally containing one or more heteroatoms belonging to groups 13-16 of the Periodic Table of the Elements, said ring optionally bearing one or more substituents; with the provisos that at least one of $R^{12}$, $R^{13}$, $R^{14}$, $R^{15}$ and $R^{16}$ is different from hydrogen atoms, and that no more than two of $T^2$, $T^3$, $T^4$, $T^5$ and $T^6$ are nitrogen atoms.

2. The metallocene compound according to claim 1 wherein M is zirconium or hafnium; X is a halogen atom, a R, OR'O or OR group; and $R^5$ and $R^6$ are a $C_1$-$C_{20}$-alkyl radical; $R^7$ and $R^8$ are $C_1$-$C_{20}$-alkyl or $C_6$-$C_{20}$-aryl radicals.

3. The metallocene compound according to claim 1 wherein in the radicals of formula (II) and (III), $T^1$ is oxygen or sulphur; $R^9$ and $R^{10}$ are a linear or branched, saturated or unsaturated $C_1$-$C_{20}$-alkyl radical or they form a condensed saturated or unsaturated 5 or 6 membered ring, optionally containing one or more heteroatoms belonging to groups 13-16 of the Periodic Table of the Elements, said ring optionally bearing one or more substituents; and $R^{11}$ is a hydrogen atom.

4. The metallocene compound according to claim 1 wherein Q is a radical of formula (IVa) bonded to the indenyl at the position indicated by the symbol *:

wherein:

$R^{14}$ is different from a hydrogen atom.

5. The metallocene compound according to claim 4 wherein $R^{14}$ is a branched, saturated or unsaturated $C_1$-$C_{20}$-alkyl or $C_6$-$C_{20}$-aryl radical.

6. The metallocene compound according to claim 1 wherein Q is a radical of formula (IVb) bonded to the indenyl at the position indicated by the symbol *:

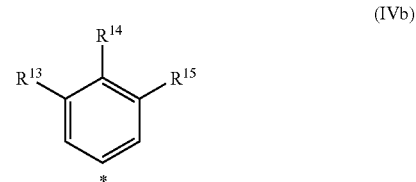

wherein:

$R^{13}$ and $R^{15}$ are different from hydrogen atoms; and $R^{14}$ is a hydrogen atom or a $R^{18}$ or $OR^{18}$ group, wherein $R^{18}$ is a linear or branched, saturated or unsaturated $C_1$-$C_{20}$-alkyl or $C_6$-$C_{20}$-aryl radical optionally containing one or more heteroatoms belonging to groups 13-17 of the Periodic Table of the Elements.

7. The metallocene compound according to claim 6 wherein $R^{13}$ and $R^{15}$ are a branched, saturated or unsaturated $C_1$-$C_{20}$-alkyl or a $CF_3$ radical; and $R^{14}$ is a hydrogen atom or a $OR^{18}$ group, wherein $R^{18}$ is a linear or branched, saturated or unsaturated $C_1$-$C_{20}$-alkyl or $C_6$-$C_{20}$-aryl radical.

8. The metallocene compound according to claim 1 wherein Q is a radical of formula (IVc) bonded to the indenyl at the position indicated by the symbol *:

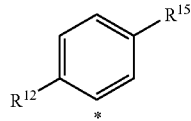

(IVc)

wherein:
$R^{12}$ and $R^{15}$ are different from hydrogen atoms.

9. The metallocene compound according to claim 8 wherein $R^{12}$ and $R^{15}$ are a linear, saturated or unsaturated $C_1$-$C_{20}$-alkyl radical.

10. The metallocene compound according to claim 1 wherein Q is a radical of formula (IVd) bonded to the indenyl at the position indicated by the symbol *:

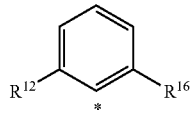

(IVd)

wherein
$R^{12}$ and $R^{16}$ are different from hydrogen atoms.

11. The metallocene compound according to claim 10 wherein $R^{12}$ and $R^{16}$ are a linear, saturated or unsaturated $C_1$-$C_{20}$-alkyl radicals.

12. The metallocene compound according to claim 1 wherein Q is a radical of formula (IVe) bonded to the indenyl at the position indicated by the symbol *:

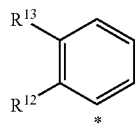

(IVe)

wherein
$R^{12}$ and $R^{13}$ are different from hydrogen atoms.

13. The metallocene compound according to claim 12 wherein $R^{12}$ and $R^{13}$ are linear, saturated or unsaturated $C_1$-$C_{20}$-alkyl radical, or they form a saturated or unsaturated condensed 5 or 6 membered ring optionally containing one or more heteroatoms belonging to groups 13-16 of the Periodic Table of the Elements, said ring optionally bearing one or more substituents.

14. The metallocene compound according to claim 12 wherein $R^{12}$ and $R^{13}$ form a saturated or unsaturated condensed 5 or 6 membered ring optionally containing one or more heteroatoms belonging to groups 13-16 of the Periodic Table of the Elements, said ring optionally bearing one or more substituents.

15. The metallocene compound according to claim 1 wherein Q is a radical of formula (IVf) being bonded to the indenyl at the position indicated by the symbol *:

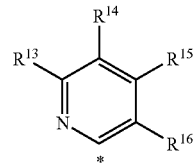

(IVf)

wherein
at least one among $R^{13}$, $R^{14}$, $R^{15}$ and $R^{16}$ is different from a hydrogen atom.

16. The metallocene compound according to claim 15 wherein $R^{15}$ and $R^{16}$ are hydrogen atoms; and $R^{13}$ and $R^{14}$ are a linear or branched, saturated or unsaturated $C_1$-$C_{20}$-alkyl radicals, or they form a saturated or unsaturated condensed 5 or 6 membered ring optionally containing one or more heteroatoms belonging to groups 13-16 of the Periodic Table of the Elements, said ring optionally bearing one or more substituents.

17. The metallocene compound according to claim 1 having formula (Ia) or (Ib):

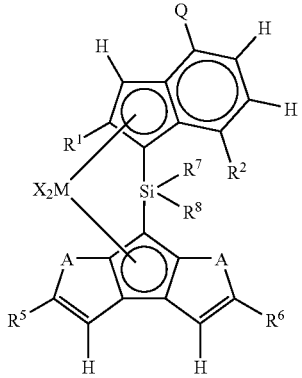

(Ia)

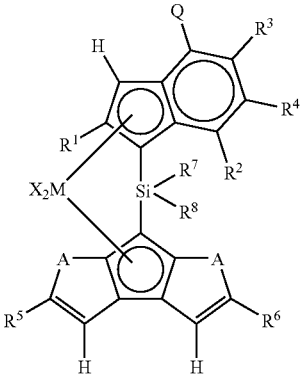

(Ib)

wherein;
$R^2$ is a linear or branched, saturated or unsaturated $C_1$-$C_{20}$-alkyl radical; and
$R^3$ and $R^4$ form together a condensed saturated 5 or 6 membered aliphatic ring.

18. A compound of formula (V)

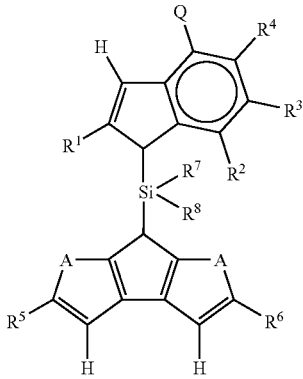

and its double bond isomer;

wherein $R^1$ is a linear $C_1$-$C_{20}$-alkyl radical;

$R^2$ is a hydrogen atom or a linear or branched, saturated or unsaturated $C_1$-$C_{20}$-alkyl radical;

$R^3$ and $R^4$, same or different, are hydrogen atoms or a linear or branched, saturated or unsaturated $C_1$-$C_{20}$, $C_3$-$C_{20}$-cycloalkyl, $C_6$-$C_{20}$-arly, $C_7$-$C_{20}$-arylalky, $C_7$-$C_{20}$-arylalkyl radicals, optionally containing one or more heteroatoms belonging to groups 13-17 of the Periodic Table of the Elements; or they can form together a condensed saturated or unsaturated 5 or 6 membered ring, optionally containing one or more heteroatoms belonging to groups 13-16 of the Periodic Table of the Elements, said ring optionally bearing one or more substituents;

$R^5$ and $R^6$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; $R^7$ and $R^8$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements;

A, same or different, is a sulphur (S) atom or an oxygen (O) atom;

Q is a radical of formula (II), (III) or (IV)) being bonded to the indenyl at the position marked with the symbol *;

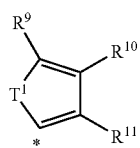

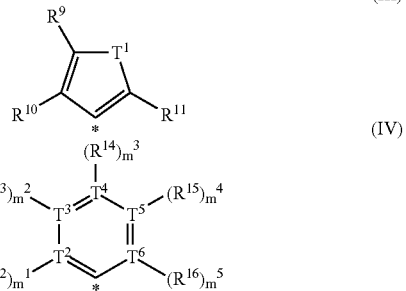

wherein:

$T^1$ is a sulphur (S) atom, an oxygen (O) atom or a NR group R being defined as above;

$R^9$, $R^{10}$ and $R^{11}$, same or different, are hydrogen atoms Or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-arylalkyl, $C_7$-$C_{20}$-arylalkyl radicals, optionally containing one or more heteroatoms belonging to groups 13-17 of the Periodic Table of the Elements; or $R^9$ and $R^{10}$ can form together a condensed saturated or unsaturated 5 or 6 membered ring, optionally containing one or more heteroatoms belonging to groups 13-16 of the Periodic Table of the Elements, said ring optionally bearing one or more substituents;

$T^2$, $T^3$, $T^4$, $T^5$ and $T^6$, same or different, are carbon atoms (C) or nitrogen atoms (N);

each of $m^1$, $m^2$, $m^3$, $m^4$ and $m^5$ is 0 when the correspondent $T^2$, $T^3$, $T^4$, $T^5$ and $T^6$ is a nitrogen atom and is 1 when the correspondent $T^2$, $T^3$, $T^4$, $T^5$ and $T^6$ is a carbon atom;

$R^{12}$, $R^{13}$, $R^{14}$, $R^{15}$ and $R^6$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or two vicinal $R^{12}$, $R^{13}$, $R^{14}$, $R^{15}$ can form together a condensed saturated or unsaturated 5 or 6 membered ring, optionally containing one or more heteroatoms belonging to groups 13-16 of the Periodic Table of the Elements, said ring optionally bearing one or more substituents; with the provisos that at least one of $R^{12}$, $R^{13}$, $R^{14}$, $R^{15}$ and $R^{16}$ is different from hydrogen atoms, and that no more than two of $T^2$, $T^3$, $T^4$, $T^5$ and $T^6$ are nitrogen atoms.

19. A catalyst for the polymerization of alpha-olefins obtainable by contacting:

a) a metallocene compound of formula (I):

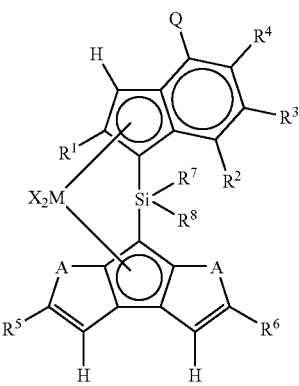

wherein

M is selected from the group consisting of zirconium, titanium and hafnium;

X, same or different, is a hydrogen atom, a halogen atom, a R, OR, OR'O, $OSO_2CF_3$, OCOR, SR, $NR_2$ or $PR_2$ group, wherein the R substituents are linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements and the R' substituent is a divalent radical selected from the group consisting of $C_1$-$C_{20}$-alkylidene, $C_6$-$C_{20}$-arylidene, $C_7$-$C_{20}$-alkylarylidene, and $C_7$-$C_{20}$-arylalkylidene;

$R^1$ is a linear $C_1$-$C_2$-alkyl radical;

$R^2$ is a hydrogen atom or a linear or branched, saturated or unsaturated $C_1$-$C_{20}$-alkyl radical;

$R^3$ and $R^4$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or they can form together a condensed saturated or unsaturated 5 or 6 membered ring, optionally containing one or more heteroatoms belonging to groups 13-16 of the Periodic Table of the Elements, said ring optionally bearing one or more substituents;

$R^5$ and $R^6$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; $R^7$ and $R^8$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements;

A, same or different, is a sulphur (S) atom or an oxygen (O) atom;

Q is a radical of formula (II), (III) or (IV)) being bonded to the indenyl at the position marked with the symbol *;

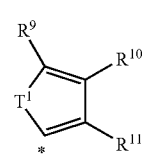
(II)

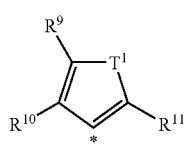
(III)

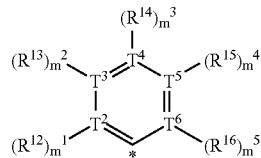
(IV)

wherein:

$T^1$ is a sulphur (S) atom, an oxygen (O) atom or a NR group R being defined as above;

$R^9$, $R^{10}$ and $R^{11}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or $R^9$ and $R^{10}$ can form together a condensed saturated or unsaturated 5 or 6 membered ring, optionally containing one or more heteroatoms belonging to groups 13-16 of the Periodic Table of the Elements, said ring optionally bearing one or more substituents;

$T^2$, $T^3$, $T^4$, $T^5$ and $T^6$, same or different, are carbon atoms (C) or nitrogen atoms (N);

each of $m^1$, $m^2$, $m^3$, $m^4$ and $m^5$ is 0 when the correspondent $T^2$, $T^3$, $T^4$, $T^5$ and $T^6$ is a nitrogen atom and is 1 when the correspondent $T^2$, $T^3$, $T^4$, $T^5$ and $T^6$ is a carbon atom;

$R^{12}$, $R^{13}$, $R^{14}$, $R^{15}$ and $R^{16}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or two vicinal $R^{12}$, $R^{13}$, $R^{14}$, $R^{15}$ can form together a condensed saturated or unsaturated 5 or 6 membered ring, optionally containing one or more heteroatoms belonging to groups 13-16 of the Periodic Table of the Elements, said ring optionally bearing one or more substituents; with the provisos that at least one of $R^{12}$, $R^{13}$, $R^{14}$, $R^{15}$ and $R^{16}$ is different from hydrogen atoms, and that no more than two of $T^2$, $T^3$, $T^4$, $T^5$ and $T^6$ are nitrogen atoms;

b) an alumoxane or a compound that forms an alkylmetallocene cation; and c) optionally an organo aluminum compound.

20. A process for polymerizing one or more alpha-olefins of formula $CH_2$=CHZ, wherein Z is a hydrogen atom or a $C_1$-$C_{20}$ alkyl group, comprising the step of contacting under polymerization conditions at least one of said aipha-olefins with a catalyst system obtained by contacting:

a) a metallocene compound of formula (I):

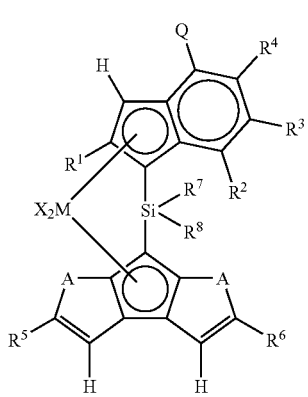
(I)

wherein

M is selected from the group consisting of zirconium, titanium and hafnium;

X, same or different, is a hydrogen atom, a halogen atom, a R, OR, OR'O, $OSO_2CF_3$, OCOR, SR, $NR_2$ or $PR_2$ group, wherein the R substituents are linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements and the R' substituent is a divalent radical selected from the group consisting of $C_1$-$C_{20}$-alkylidene, $C_6$-$C_{20}$-arylidene, $C_7$-$C_{20}$-alkylarylidene, and $C_7$-$C_{20}$-arylalkylidene;

$R^1$ is a linear $C_1$-$C_2$-alkyl radical $R^2$ is a hydrogen atom or a linear or branched, saturated or unsaturated $C_1$-$C_{20}$-alkyl radical;

$R^3$ and $R^4$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or they can form together a condensed saturated or unsaturated 5 or 6 membered ring, optionally containing one or more heteroatoms belonging to groups 13-16 of the Periodic Table of the Elements, said ring optionally bearing one or more substituents;

$R^5$ and $R^6$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; $R^7$ and $R^8$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements;

A, same or different, is a sulphur (S) atom or an oxygen (O) atom;

Q is a radical of formula (II), (III) or (IV)) being bonded to the indenyl at the position marked with the symbol *;

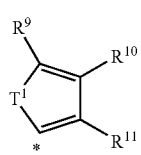
(II)

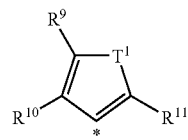
(III)

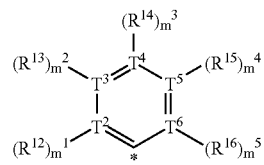
(IV)

wherein:

$T^1$ is a sulphur (S) atom, an oxygen (O) atom or a NR group R being defined as above;

$R^9$, $R^{10}$ and $R^{11}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-arylalkyl, $C_7$-$C_{20}$-arylalkyl radicals, optionally containing one or more heteroatoms belonging to groups 13-17 of the Periodic Table of the Elements; or $R^9$ and $R^{10}$ can form together a condensed saturated or unsaturated 5 or 6 membered ring, optionally containing one or more heteroatoms belonging to groups 13-16 of the Periodic Table of the Elements, said ring optionally bearing one or more substituents;

$T^2$, $T^3$, $T^4$, $T^5$ and $T^6$, same or different, are carbon atoms (C) or nitrogen atoms (N);

each of $m^1$, $m^2$, $m^3$, $m^4$ and $m^5$ is 0 when the correspondent $T^2$, $T^3$, $T^4$, $T^5$ and $T^6$ is a nitrogen atom and is 1 when the correspondent $T^2$, $T^3$, $T^4$, $T^5$ and $T^6$ is a carbon atom;

$R^{12}$, $R^{13}$, $R^{14}$, $R^{15}$ and $R^{16}$, same or different, are hydrogen atoms or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, $C_7$-$C_{20}$-arylalkyl radicals, optionally containing one or more heteroatoms belonging to groups 13-17 of the Periodic Table of the Elements; or two vicinal $R^{12}$, $R^{13}$, $R^{14}$, $R^{15}$ can form together a condensed saturated or unsaturated 5 or 6 membered ring, optionally containing one or more heteroatoms belonging to groups 13-16 of the Periodic Table of the Elements, said ring optionally bearing one or more substituents; with the provisos that at least one of $R^{12}$, $R^{13}$, $R^{14}$, $R^{15}$ and $R^{16}$ is different from hydrogen atoms, and that no more than two of $T^2$, $T^3$, $T^4$, $T^5$ and $T^6$ are nitrogen atoms;

b) at least one alumoxane or compounds that form an alkylmetallocene cation; and c) optionally an organo aluminum compound.

21. The process according to claim 20 wherein the alpha-olefins are selected from the group consisting of ethylene, propylene and 1-butene.

22. The process according to claim 20 wherein propylene is copolymerized with ethylene or higher alpha-olefins.

23. The process according to claim 20 wherein ethylene is copolymerized with higher alpha-olefins.

* * * * *